(12) United States Patent
McGee et al.

(10) Patent No.: US 10,906,903 B2
(45) Date of Patent: *Feb. 2, 2021

(54) SYNTHETIC METHODS FOR PREPARATION OF (S)-(2R,3R,11BR)-3-ISOBUTYL-9,10-DIMETHOXY-2,3,4,6,7,11B-HEXAHYDRO-1H-PYRIDO[2,1,-A]ISOQUINOLIN-2-YL 2-AMINO-3-METHYLBUTANOATE DI(4-METHYLBENZENESULFONATE)

(71) Applicant: Neurocrine Biosciences, Inc., San Diego, CA (US)

(72) Inventors: Kevin McGee, San Diego, CA (US); Bin-Feng Li, Suzhou Industrial Park (CN); Shawn Branum, San Diego, CA (US)

(73) Assignee: Neurocrine Biosciences, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/929,714

(22) Filed: Jul. 15, 2020

(65) Prior Publication Data

US 2020/0347056 A1 Nov. 5, 2020

Related U.S. Application Data

(63) Continuation of application No. 16/509,552, filed on Jul. 12, 2019, which is a continuation of application No. 16/196,234, filed on Nov. 20, 2018, now abandoned, which is a continuation of application No. 15/388,960, filed on Dec. 22, 2016, now Pat. No. 10,160,757.

(60) Provisional application No. 62/387,442, filed on Dec. 23, 2015.

(51) Int. Cl.
*C07D 471/06* (2006.01)
*A61K 31/4745* (2006.01)
*C07D 471/04* (2006.01)

(52) U.S. Cl.
CPC .................. *C07D 471/04* (2013.01)

(58) Field of Classification Search
CPC .......................... C07D 471/06; A61K 31/4745
USPC ............................................. 546/95; 514/294
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,328,245 A | 5/1982 | Yu et al. | |
| 4,409,239 A | 10/1983 | Yu | |
| 4,410,545 A | 10/1983 | Yu et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,591,767 A | 1/1997 | Mohr et al. | |
| 5,612,059 A | 3/1997 | Cardinal et al. | |
| 5,639,476 A | 6/1997 | Oshlack et al. | |
| 5,639,480 A | 6/1997 | Bodmer et al. | |
| 5,674,533 A | 10/1997 | Santus et al. | |
| 5,698,220 A | 12/1997 | Cardinal et al. | |
| 5,709,874 A | 1/1998 | Hanson et al. | |
| 5,733,566 A | 3/1998 | Lewis | |
| 5,739,108 A | 4/1998 | Mitchell | |
| 5,759,542 A | 6/1998 | Gorewich | |
| 5,798,119 A | 8/1998 | Herbig et al. | |
| 5,840,674 A | 11/1998 | Yatvin et al. | |
| 5,891,474 A | 4/1999 | Busetti et al. | |
| 5,900,252 A | 5/1999 | Calanchi et al. | |
| 5,922,356 A | 7/1999 | Koseki et al. | |
| 5,972,366 A | 10/1999 | Heynes et al. | |
| 5,972,891 A | 10/1999 | Kamei et al. | |
| 5,980,945 A | 11/1999 | Ruiz | |
| 5,985,307 A | 11/1999 | Hanson et al. | |
| 5,993,855 A | 11/1999 | Yoshimoto et al. | |
| 6,004,534 A | 12/1999 | Langer et al. | |
| 6,039,975 A | 3/2000 | Shah et al. | |
| 6,045,830 A | 4/2000 | Igari et al. | |
| 6,048,736 A | 4/2000 | Kosak | |
| 6,060,082 A | 5/2000 | Chen et al. | |
| 6,071,495 A | 6/2000 | Unger et al. | |
| 6,087,324 A | 7/2000 | Igari et al. | |
| 6,113,943 A | 9/2000 | Okada et al. | |
| 6,120,751 A | 9/2000 | Unger | |
| 6,131,570 A | 10/2000 | Schuster et al. | |
| 6,139,865 A | 10/2000 | Friend et al. | |
| 6,197,350 B1 | 3/2001 | Yamagata et al. | |
| 6,248,363 B1 | 6/2001 | Patel et al. | |
| 6,253,872 B1 | 7/2001 | Neumann | |
| 6,264,970 B1 | 7/2001 | Hata et al. | |
| 6,267,981 B1 | 7/2001 | Okamoto et al. | |

(Continued)

FOREIGN PATENT DOCUMENTS

| | | |
|---|---|---|
| CN | 1980942 | 6/2007 |
| EP | 1716145 | 11/2006 |

(Continued)

OTHER PUBLICATIONS

U.S. Appl. No. 16/929,694, McGee et al., filed Jul. 15, 2020.

(Continued)

*Primary Examiner* — Charanjit Aulakh

(74) *Attorney, Agent, or Firm* — Fish & Richardson P.C.

(57) ABSTRACT

Provided herein are processes for the preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a solvate, hydrate, or polymorph thereof.

30 Claims, No Drawings

(56) References Cited

U.S. PATENT DOCUMENTS

| | | |
|---|---|---|
| 6,271,359 B1 | 8/2001 | Norris et al. |
| 6,274,552 B1 | 8/2001 | Tamarkin et al. |
| 6,316,652 B1 | 11/2001 | Steliou |
| 6,350,458 B1 | 2/2002 | Modi |
| 6,376,461 B1 | 4/2002 | Igari et al. |
| 6,419,961 B1 | 7/2002 | Igari et al. |
| 6,589,548 B1 | 7/2003 | Oh et al. |
| 6,613,358 B2 | 9/2003 | Randolph et al. |
| 6,699,500 B2 | 3/2004 | Okada et al. |
| 8,039,627 B2 | 10/2011 | Gano |
| 8,357,697 B2 | 1/2013 | Gano |
| 8,524,733 B2 | 9/2013 | Gant et al. |
| 9,714,246 B2 | 7/2017 | Ashweek et al. |
| 9,782,398 B2 | 10/2017 | Hoare |
| 10,065,952 B2 | 9/2018 | McGee et al. |
| 10,160,757 B2 | 12/2018 | McGee et al. |
| 10,689,380 B1 | 6/2020 | Lopez |
| 2006/0051345 A1 | 3/2006 | Frohna |
| 2006/0241082 A1 | 10/2006 | Fleckenstein et al. |
| 2008/0108645 A1 | 5/2008 | Tridgett et al. |
| 2008/0167337 A1 | 7/2008 | Gano |
| 2009/0209755 A1 | 8/2009 | Suzuki et al. |
| 2010/0076087 A1 | 3/2010 | Gant et al. |
| 2011/0053866 A1 | 3/2011 | Duffield et al. |
| 2012/0003330 A1 | 1/2012 | Gant et al. |
| 2012/0077839 A1 | 3/2012 | Gano et al. |
| 2014/0187505 A1 | 7/2014 | Pollard |
| 2014/0341994 A1 | 11/2014 | Sommer et al. |
| 2015/0004231 A1 | 1/2015 | Sommer et al. |
| 2015/0025086 A1 | 1/2015 | Dressman et al. |
| 2016/0030414 A1 | 2/2016 | Gant et al. |
| 2016/0339011 A1 | 11/2016 | Hoare et al. |
| 2016/0346200 A1 | 12/2016 | Sommer et al. |
| 2016/0346270 A1 | 12/2016 | Stamler |
| 2017/0071932 A1 | 3/2017 | O'Brien |
| 2017/0145008 A1 | 5/2017 | McGee et al. |
| 2017/0183346 A1 | 6/2017 | McGee et al. |
| 2018/0085364 A1 | 3/2018 | Hoare |
| 2018/0280374 A1 | 10/2018 | Duffield et al. |
| 2019/0015396 A1 | 1/2019 | O'Brien et al. |
| 2019/0381016 A1 | 12/2019 | O'Brien et al. |
| 2019/0381029 A1 | 12/2019 | Hoare et al. |
| 2020/0078352 A1 | 3/2020 | O'Brien et al. |
| 2020/0093808 A1 | 3/2020 | O'Brien et al. |
| 2020/0101063 A1 | 4/2020 | O'Brien et al. |
| 2020/0179352 A1 | 6/2020 | O'Brien |
| 2020/0181140 A1 | 6/2020 | McGee et al. |
| 2020/0206215 A1 | 7/2020 | Hoare et al. |
| 2020/0230127 A1 | 7/2020 | O'Brien et al. |
| 2020/0268724 A1 | 8/2020 | O'Brien et al. |
| 2020/0268725 A1 | 8/2020 | O'Brien et al. |
| 2020/0268743 A1 | 8/2020 | O'Brien et al. |
| 2020/0268744 A1 | 8/2020 | O'Brien et al. |
| 2020/0268745 A1 | 8/2020 | O'Brien et al. |
| 2020/0276184 A1 | 9/2020 | Moore, Jr. et al. |
| 2020/0338066 A1 | 10/2020 | O'Brien et al. |
| 2020/0339574 A1 | 10/2020 | McGee et al. |
| 2020/0339575 A1 | 10/2020 | McGee et al. |
| 2020/0339576 A1 | 10/2020 | McGee et al. |

FOREIGN PATENT DOCUMENTS

| | | |
|---|---|---|
| JP | 57-077697 | 5/1982 |
| JP | 57-209225 | 12/1982 |
| WO | WO 1991/019498 | 12/1991 |
| WO | WO 1998/011897 | 3/1998 |
| WO | WO 2000/024399 | 5/2000 |
| WO | WO 2002/017918 | 3/2002 |
| WO | WO 2005/077946 | 5/2005 |
| WO | WO 2007/017654 | 2/2007 |
| WO | WO 2008/058261 | 5/2008 |
| WO | WO 2009/056885 | 5/2009 |
| WO | WO 2010/018408 | 2/2010 |
| WO | WO 2010/026435 | 3/2010 |
| WO | WO 2010/026436 | 3/2010 |
| WO | WO 2010/044961 | 4/2010 |
| WO | WO 2010/044981 | 4/2010 |
| WO | WO 2011/019956 | 2/2011 |
| WO | WO 2011/153157 | 12/2011 |
| WO | WO 2014/047167 | 3/2014 |
| WO | WO 2014/120654 | 8/2014 |
| WO | WO 2015/077521 | 5/2015 |
| WO | WO 2015/112707 | 7/2015 |
| WO | WO 2015/120110 | 8/2015 |
| WO | WO 2015/120317 | 8/2015 |
| WO | WO 2015/171802 | 11/2015 |
| WO | WO 2016/127133 | 8/2016 |
| WO | WO 2016/144901 | 9/2016 |
| WO | WO 2016/210180 | 12/2016 |
| WO | WO 2017/075340 | 5/2017 |
| WO | WO 2018/102673 | 6/2018 |
| WO | WO 2018/140092 | 8/2018 |
| WO | WO 2018/140093 | 8/2018 |
| WO | WO 2018/140094 | 8/2018 |
| WO | WO 2018/140095 | 8/2018 |
| WO | WO 2018/140096 | 8/2018 |
| WO | WO 2018/200605 | 11/2018 |
| WO | WO 2019/060322 | 3/2019 |
| WO | WO 2019/074492 | 4/2019 |
| WO | WO 2019/241555 | 12/2019 |
| WO | WO 2020/037022 | 2/2020 |

OTHER PUBLICATIONS

U.S. Appl. No. 16/929,696, McGee et al., filed Jul. 15, 2020.
U.S. Appl. No. 16/929,716, McGee et al., filed Jul. 15, 2020.
Boldt et al., "Synthesis of (+)- and (−)-Tetrabenazine from the Resolution of [alpha]-Dihydrotetrabenazine," Synthetic Communications, 2009, 39(20):3574-3585.
Foster et al., "Deuterium isotope effects in studies of drug metabolism," Adv. Drug Res., vol. 14: 1-36 (1985).
Gately et al., "Deuterioglucose: Alteration of Biodistribution by an Isotope Effect," J. Nucl. Med., 27: 388-394 (1986).
Gordon et al., "The Metabolism of the Abortifacient Terpene, (R)-(+)-Pulegone, to a Proximate Toxin, Menthofuran," Drug Metab. Dispos., 15: 589-594 (1987).
Gottlieb et al., "NMR Chemical Shifts of Common Laboratory Solvents as Trace Impurities," J. Org. Chem. 1997, 62 (21): 7512-7515.
Kenney et al., "Tetrabenazine in the treatment of hyperkinetic movement disorders," Expert Review Neurotherapeutics, 6: 7-17 (2006).
Kilbourn et al., "Absolute Configuration of (+)-alpha-Dihydrotetrabenazine, an Active Metabolite of Tetrabenazine," Chirality, 9: 59-62 (1997).
Kushner et al., "Pharmacological uses and perspectives of heavy water and deuterated compounds," Can. J. Physiol. Pharmacol., vol. 77: 79-88 (1999).
Lijinksy et al., "Dose-Response Studies in Carcinogenesis by Nitroso-N-Methyl-N-(2-Phenyl)Ethylamine in Rats and the Effects of Deuterium Substitution," Food Cosmet. Toxicol, 20:393-399 (1982).
Lijinksy et al., "Dose-Response Studies With Nitrosoheptamethyleneimine and its alpha-Deuterium-Labeled Derivative in F344 Rats," J. Nat. Cancer Inst., 69: 1127-1133 (1982).
Mangold et al., "Effects of deuterium labeling on azido amino acid nutagenicity in *Salmonella typhimurium*," Mutation Res., 308: 33-42 (1994).
Muller, "Valbenazine granted breakthrough drug status for treating tardive dyskinesia," Expert Opin. Investig. Drugs, 24: 737-742 (2015).
Wade D, "Deuterium isotope effects on noncovalent interactions between molecules," Chem. Biol. Interact. 117: 191-217 (1999).
Zello et al., "Plasma and Urine Enrichments Following Infusion of L-[1-13C]phenylalanine and L-[ring-2H5]phenylalanine in Humans: Evidence for an Isotope Effect in Renal Tubular Reabsorption," Metabolism, 43: 487 (1994).
U.S. Appl. No. 17/005,425, O'Brien, filed Aug. 28, 2020.
U.S. Appl. No. 17/021,362, O'Brien et al., filed Sep. 15, 2020.

(56) References Cited

OTHER PUBLICATIONS

Cummings et al., "Deuterium tetrabenazine for tardive dyskinesia," Clinical Schizophrenia & Related Psychoses, 2018, 214-220.
Preswick Pharmaceuticals et al., "Xenazine (tetrabenazine) tablets," 2008, retrieved from URL: https://accessdata.fda.gov/drugsatfda_docs/label/2011/021894s0051bl.pdj, retrieved on Jul. 28, 2020, 27 pages.
U.S. Appl. No. 16/481,033, O'Brien et al., filed Jul. 25, 2019.
U.S. Appl. No. 16/481,034, O'Brien et al., filed Jul. 25, 2019.
U.S. Appl. No. 16/481,037, O'Brien et al., filed Jul. 25, 2019.
U.S. Appl. No. 16/509,552, McGee et al., filed Jul. 12, 2019.
U.S. Appl. No. 16/608,521, O'Brien, filed Oct. 25, 2019.
U.S. Appl. No. 16/646,866, Moore Jr. et al., filed Mar. 12, 2020.
U.S. Appl. No. 16/651,887, O'Brien et al., filed Mar. 27, 2020.
U.S. Appl. No. 16/662,346, McGee et al., filed Oct. 24, 2019.
U.S. Appl. No. 16/701,339, O'Brien et al., filed Dec. 3, 2019.
U.S. Appl. No. 16/754,658, O'Brien et al., filed Apr. 8, 2020.
U.S. Appl. No. 16/817,723, Hoare et al., filed Mar. 13, 2020.
U.S. Appl. No. 16/845,134, O'Brien et al., filed Apr. 10, 2020.
U.S. Appl. No. 16/870,572, O'Brien et al., filed May 8, 2020.
U.S. Appl. No. 16/871,528, O'Brien et al., filed May 11, 2020.
U.S. Appl. No. 16/983,334, Liang et al., filed Aug. 3, 2020.
U.S. Appl. No. 16/989,206, Loewen et al., filed Aug. 10, 2020.
U.S. Appl. No. 17/074,278, Moore Jr. et al., filed Oct. 19, 2020.
U.S. Appl. No. 17/074,383, Moore Jr. et al., filed Oct. 19, 2020.
"Cytochrome P450 Oxidoreductase (POR) Deficiency," GeneDx, 2016, 5 pages.
"Neurocrine Valbenazine," Science IP Order 3198386, Oct. 2, 2019, 92 pages.
[No Author Listed], "Cytochrome P450 3A4 and 3A5 known drug interaction chart," 2014, 2 pages.
[No Author Listed], "Drug interactions with CYP3A inducers and inhibitors for Torisel (temsirolimus) injection," Wyeth Pharmaceuticals, 2008, 12 pages.
[No Author Listed], "Physician guidelines: drugs metabolized by cytochrome P450's," Genelex Corporation, 2005, 4 pages.
[No Author Listed],"Ingrezza Prescription Information," Neurocrine Biosciences, Apr. 2017, 16 pages.
Anonymous, "11th Annual Meeting Schedule," ASENT, Mar. 5-7, 2009, 3 pages.
Anonymous, "12th Annual Meeting Program," ASENT, Bethesda, Maryland, Mar. 4-6, 2010, 1 page.
Anonymous, "Neurocrine Announces Phase IIb Results of VMAT2 Inhibitor NBI-98854 for Treatment of Tardive Dyskinesia," Neurocrine Biosciences: Investors: PressRelease, Sep. 9, 2013, [retrieved on Dec. 13, 2018] retrieved from URL<http://phoenix.corporate-ir.net/phoenix.zhtml?c=68817&p=irol-newsArticle_Print&ID=1853185>, 7 pages.
Australian Office Action in AU Appln. No. 2015256012, dated May 26, 2020, 5 pages.
Ballard et al., "Management of Agitation and Aggression Associated with Alzheimer's disease: controversies and possible solutions," Curr Opin in Psych., Nov. 2009, 22(6):532-540.
Ballard et al., "Neuroleptic drugs in dementia: benefits and harm," Nat Rev Neurosci., Jun. 2006, 7:492-500.
Ballard et al., "Quetiapine and rivastigmine and cognitive decline in Alzheimer's disease: randomised double blind placebo controlled trial," BMJ, Apr. 16, 2005, 330:874-877.
Bastin et al., "Salt Selection and Optimisation Procedures for Pharmaceutical New Chemical Entities," Organic Process Res. Dev., 2000, 4(5):427-435.
Bauer, "Pharmaceutical Solids—The Amorphous Phase," J Validation Tech., 2009, 15(3):63-68.
Berge et al., "Pharmaceutical Salts," J Pharm Sci., Jan. 1977, 66(1):1-19.
Bhidayasiri and Boonyawairoj, "Spectrum of tardive syndromes: clinical recognition and management.," Postgrad Med J, Feb. 2011, 87(1024): 132-141.
Brunner et al., "Comprehensive Analysis of the 16p11.2 Deletion and Null Cntnap2 Mouse Models of Autism Spectrum Disorder," PLoS One, Aug. 14, 2015, 10(8):e0134572.
Brusa et al., "Tetrabenazine improves levodopa-induced peak-dose dyskinesias in patients with Parkinson's disease," Funct. Neural., 2013, 28(2):101-5.
Bystritsky, "Treatment-resistant anxiety disorders," Mol. Psychiatry, Sep. 2006, 11(9):805-814.
Caira et al., "Crystalline Polymorphism of Organic Compounds," Topics in Current Chemistry, 1998, 198(36):163-208.
Caroff et al., "Treatment of tardive dyskinesia with tetrabenazine or valbenazine: a systematic review," J. Com. Eff. Research, 2017, 7(2):135-148.
Center for Drug Evaluation and Research Application No. 2092410 ("Publication No. 2092410"), Clinical Pharmacology and Biopharmaceuticals Review, Submission Date Aug. 11, 2016.
Chinese Office Action in Chinese Application No. 201580023821.X, dated Jun. 20, 2018, 10 pages.
Citrome, "Reprint of: Clinical management of tardive dyskinesia: five steps to success," Journal of Neurological Sciences, 2018, 389:61-66.
Citrome, "Valbenazine for tardive dyskinesia: A systematic review of the efficacy and safety profile for this newly approved novel medication—What is the number needed to treat, number needed to harm and likelihood to be helped or harmed?," Int J Clin Pract., 2017, e12964.
Cohen-Mansfield et al., "A description of agitation in a nursing home," J Gerontol., May 1989, 44(3):M77-M84.
Correll and Schenk, "Tardive dyskinesia and new antipsychotics," Curr Opin Psychiatry, Mar. 2008, 21(2):151-156.
Corvin, "Two patients walk into a clinic . . . a genomics perspective on the future of schizophreniam," BMC Biol., 2011, 8 pages.
Cummings et al., "The Neuropsychiatric Inventory: comprehensive assessment of psychopathology in dementia," Neurology, 1994, 44:2308-2314.
Davis et al., "Center For Drug Evaluation And Research," Medical Reviews(s), 2017, Accessed on Sep. 30, 2020, retrieved from URL<https://www.accessdata.fda.gov/drugsatfda_docs/nda/2017/209241Orig1s000MedR.pdf>, 297 pages.
Derangula et al, "Liquid chromatography-tandem mass spectrometric assay for the determination of tetrabenazine and its active metabolites in human plasma: a pharmacokinetic study," Biomedical Chromatography, Jun. 2013, 27(6):792-801.
Drug Development and Drug Interactions: Table of Substrates, Inhibitor and Inducers at https://www.fda.gov/drugs/developmentapprovalprocess/developmentesources/druginteractionslabeling/ucm093664.htm, U.S. Food and Drug Administration, 2017, 18 pages.
Erickson et al., "Reserpine- and tetrabenazine-sensitive transport of (3)H-histamine by the neuronal isoform of the vesicular monoamine transporter," Journal of Molecular Neuroscience, 1995, 6(4):277-287.
Eurasian Office Action in Eurasian Application No. 201890108, Dated Oct. 30, 2018, 5 pages.
European Office Action in European Application No. 15734438.5, dated Jul. 17, 2018, 4 pages.
Extended European Search Report in European Appln. No. 16734150.2, dated Apr. 11, 2019, 7 pages.
Fahr, "Kapseln," Pharmazeutische Technologie, Jan. 2000, p. 237 (with machine English translation).
Fda.gov [online], U.S. Food & Drug Administration Drug Approvals and Databases, "Ingrezza (valbenazine) Capsules," dated Jun. 1, 2017, retrieved on Sep. 30, 2020, retrieved from URL<https://www.accessdata.fda.gov/drugsatfda_docs/nda/2017/209241Orig1s000TOC.cfm>, 2 pages.
Fields et al., "Pill Properties that Cause Dysphagia and Treatment Failure," Current Therapeutic Research, Aug. 2015, 77:79-82.
Gantois et al., "Restoring the phenotype of fragile X syndrome: insight from the mouse model," Curr Mol Med., Sep. 2001, 1(4):447-455.
Grigoriadis et al., "Pharmacologic characterization of valbenazine (NBI-98854) and its metabolites," Journal of Pharmacology and Experimental Therapeutics, 2017, 361(3):454-461.

(56) References Cited

OTHER PUBLICATIONS

Guilloteau et al., "PET and SPECT exploration of central monoaminergic transporters for the development of new drugs and treatments in brain disorders," Current Pharmaceutical Design, Jan. 1, 2005, 11(25):3237-3245.

Gulieva et al., "Neuropharmacology analysis of the effect of olanzapine and clozapine on behavior characteristics and neuromodulator content in rat brain structure," Psychopharmacology and biological necrology, 2004, 585-589.

Guridi et al., "Clinical Features, Pathophysiology, and Treatment of Levodopa-Induced Dyskinesias in Parkinson's Disease," Parkinson's Disease, 2012, 1-15.

Harriot et al., "Identification of the First Selective Small Molecule BB2 Antagonists," Poster, Presented at the 249th ACS National Meeting & Exposition, Denver CO, Mar. 22-26, 2015, 1 page.

Hassan et al., "Drug use and dosing in chronic kidney disease," Annals of the Academy of Medicine, 2009, 38(12):1095-1103.

Hauser et al., "KINECT 3: A phase 3 randomized, double-blind, placebo-controlled trial of valbenazine for tardive dyskinesia," American Journal of Psychiatry, 2016, 174(5):476-484.

Healy et al., "Clozapine-reserpine combination for refractory psychosis," Schizophrenia Research, Jan. 1, 1997, 25:259-260.

Herrmann et al., "A Placebo-Controlled Trial of Valproate for Agitation and Aggression in Alzheimer's Disease," Dement Geriatr Cogn Disord., Jan. 2007, 23:116-119.

Hoare et al., "Conformational states of the corticotropin releasing factor 1 (CRF1) receptor: detection, and pharmacological evaluation by peptide ligands," Peptides, Dec. 2003, 24(12):1881-1897.

Horev et al., "Dosage-dependent phenotypes in models of 16p11.2 lesions found in autism," Proc Natl Acad Sci USA., 2011, 108(41):17076-17081.

Howard et al., "Guidelines for the management of agitation in dementia," Int. J. Geriatr. Psychiatry, Jul. 2001, 16(7):714-717.

Hu, "New Fluorescent Substrate Enables Quantitative and High-throughput Examination of Vesicular Monoamine Transporter 2 (VMAT2)," ACS Chem Biol. Sep. 20, 2013:8(9):1947-1954.

Ingrezza, Highlights of Prescribing Information, Neurocrine Biosciences, Inc., revised Oct. 2017, 15 pages.

Ingrezza, Patient Information, Neurocrine Biosciences, Inc., revised Oct. 2017, 1 page.

International Preliminary Report on Patentability in Appln. No. PCT/US2017/055907, dated Apr. 14, 2020, 18 pages.

International Preliminary Report on Patentability in Appln. No. PCT/US2017/055947, dated Apr. 23, 2020, 10 pages.

International Preliminary Report on Patentability in Appln. No. PCT/US2018/029255, dated Oct. 29, 2019, 7 pages.

International Preliminary Report on Patentability in International Application No. PCT/US2016/039098, dated Dec. 26, 2017, 8 pages.

International Preliminary Report on Patentability in International Application No. PCT/US2017/055877, dated Jul. 30, 2019, 11 pages.

International Preliminary Report on Patentability in International Application No. PCT/US2017/055931, dated Jul. 30, 2019, 16 pages.

International Preliminary Report on Patentability in International Application No. PCT/US2017/055965, dated Jul. 30, 2019, 8 pages.

International Preliminary Report on Patentability in International Application No. PCT/US2017/055980, dated Jul. 30, 2019, 7 pages.

International Preliminary Report on Patentability in International Appln. No. PCT/US2017/064196, dated Jun. 4, 2019, 6 pages.

International Report on Patentability in International Application No. PCT/US2015/029519, dated Nov. 8, 2016, 8 pages.

International Search Report and Written Opinion in Appln. No. PCT/US2017/055877, dated Dec. 26, 2019, 11 pages.

International Search Report and Written Opinion in Appln. No. PCT/US2017/055907, dated Dec. 5, 2017, 21 pages.

International Search Report and Written Opinion in Appln. No. PCT/US2017/055931, dated Dec. 11, 2017, 17 pages.

International Search Report and Written Opinion in Appln. No. PCT/US2017/55965, dated Dec. 5, 2017, 9 pages.

International Search Report and Written Opinion in Appln. No. PCT/US2018/029255, dated Jun. 26, 2018, 9 pages.

International Search Report and Written Opinion in Appln. No. PCT/US2017/55980, dated Dec. 1, 2017, 9 pages.

International Search Report and Written Opinion in International Application No. PCT/US2015/029519, dated Jun. 21, 2015, 11 pages.

International Search Report and Written Opinion in International Application No. PCT/US2016/039098, dated Nov. 22, 2016, 15 pages.

International Search Report and Written Opinion in International Appln. No. PCT/US2017/064196, dated Feb. 21, 2018, 10 pages.

International Search Report and Written Opinion in International Appln. No. PCT/US2019/46462, dated Nov. 7, 2019, 14 pages.

International Search Report and Written Opinion in International Appln. No. PCT/US2020/047392, dated Oct. 26, 2020, 18 pages.

International Search Report in Appln. No. PCT/US2017/055947, dated Dec. 5, 2017, 8 pages.

Jacq et al., "Development and validation of an automated static headspace gas chromatography-mass spectrometry (SHS-GC-MS) method for monitoring the formation of ethyl methane sulfonate from ethanol and methane sulfonic acid," J Pharm. Biomed Anal., 2008, 48(5):1339-1344.

Jankovic and Beach, "Long-term effects of tetrabenazine in hyperkinetic movement disorders," Neurology, Feb. 1, 1997, 48(2):359-362.

Jankovic et al., "Lesch-Nyhan Syndrome. A Study of Motor Behaviour and Cerebrospinal Fluid Neurotransmitters," Ann Neuro., May 1988, 23(5):466-469.

Jankovic., "Dopamine depleters in the treatment of hyperkinetic movement disorders," Expert Opinion on Pharmacotherapy, 17.18, 2016, 2461-2470.

Japanese Office Action in Japanese Application No. 2016-566238, dated Feb. 12, 2019, 13 pages.

Jiang, "Application of Deuteration in Drug Research," Qilu Pharmacautical Affairs, 2010, 29(11):682-684.

Jinnah et al., "Amphetamine-induced behavioral phenotype in a hypoxanthine-guanine phosphoribosyltransferase-deficient mouse model of Lesch-Nyhan syndrome," Behav Neurosci., Dec. 1991, 105(4):1004-1012.

Josiassen et al., "Long-term safety and tolerability of valbenazine (NBI-98854) in subjects with tardive dyskinesia and a diagnosis of Schizophrenia or mood disorder," Psychopharmacology Bulletin, 2017, 47(3):61-68.

Jul et al., "Hyperactivity with Agitative-Like Behavior in a Mouse Tauopathy Model," J Alzheimer's Dis., 2015, 49(3):783-795.

Katz et al., "Preclinical research in Rett syndrome: setting the foundation for translational success," Disease Models & Mechanisms, 2012, 5:733-745.

Kay et al., "The Positive and Negative Syndrome Scale (PANSS) for Schizophrenia," Schizophrenia Bulletin, 1987, 13:262-276.

Kazdoba et al., "Modeling fragile X syndrome in the Fmr1 knockout mouse," Intractable Rare Dis Res., Nov. 2014, 3(4):118-133.

Kenney et al., "Long-Term Tolerability of Tetrabenazine in the Treatment of Hyperkinetic Movement Disorders," Movement Disorders, 2007, 22(2):193-197.

Khalsa et al., "Treatment-resistant OCD: Options beyond first-line medications," Curr. Psychiatry, 2011, 10(11):45-52.

Kilbourn et al., "Binding of alpha-dihydrotetrabenazine to the vesicular monoamine transporter is stereospecific," Eur J Pharmacol May 24 1995, 278(3):249-252.

Kilbourn et al., "In vivo binding of (+)-alpha-[3H]dihydrotetrabenazine to the vesicular monoamine transporter of rat brain: bolus vs. equilibrium studies," European Journal of Pharmacology, 1997, 331(2-3):161-168.

Kilbourn et al., "In vivo measures of dopaminergic radioligands in the rat brain: equilibrium infusion studies," Synapse, Mar. 1, 2002, 43(3):188-194.

Kim, "Valbenazine: First Global Approval," Drugs, 2017, 77:1123-1129.

(56) References Cited

OTHER PUBLICATIONS

Kimiagar er al., "Rapid improvement of tardive dyskinesia with tetrabenazine, clonazepam and clozapine combined: a naturalistic long-term follow-up study," J Neurol., Nov. 9, 2011, 259(4):660-664.
Koch et al., "Successful Therapy of Tardive Dyskinesia in a 71-year-old Woman with a combination of Tetrabenazine, Olanzapine and Tiapride," IJCP, Mar. 1, 2003, 57(2):147-149.
Kuehn et al., "A potential animal model for Lesch-Nyhan syndrome through introduction of HPRT mutations into mice," Nature, Mar. 1987, 326(6110):295-298.
Kurlan, "Treatment of Tourette Syndrome," Neurotherapeutics, 2014, 11:161-165.
Lee et al., "In vitro and in vivo studies of benzisoquinoline ligands for the brain synaptic vesicle monoamine transporter," J. Med Chem., Jan. 5, 1996, 39(1):191-196.
Loewen et al., "Evaluation of the potential for concomitant medications to affect valbenazine pharmacokinetics," Poster, Presented at the American Society of Clinical Psychopharmacology, May 29-Jun. 2, 2017: Miami, FL, 1 page.
Loewen et al., "Evaluation of the potential for valbenzaine to elicit drug interactions," Poster, Presented at The American Society of Clinical Psychopharmacology, May 29-Jun. 2, 2017: Miami, FL, 1 page.
Lombroso et al., "Tourette Syndrome and Obsessive-Compulsive Disorder ," Brain Dev., 2008, 30(4): 231-237.
Loriot et al., "Drug insight: gastrointestinal and hepatic adverse effects of molecular-targeted agents in cancer therapy," Nature Clinical Practice Oncology, 2008, 5(5):268-278.
Luo et al., "Single dose and repeat once-daily dose safety, tolerability, and pharmacokinetics of valbenazine in healthy male subjects," Poster, Presented at The American Psychiatric Association Annual Meeting, May 20-24, 2017, San Diego, CA, 1 page.
Madan, Invited Speaker, "NBI-98854: Human pharmacokinetics of NBI-98854 a selective inhibitory of VMAT2 with an attractive PK and safety profile for hyperkinetic movement disorders," Pipeline Projects Session, 12th annual meeting of American Society for Experimental NeuroTherapeutics, Bethesda, MD, 2010, 5 slides.
Madan, Invited Speaker, "NBI-98854: Selective inhibitor of VMAT2 with an attractive PK and safety profile for hyperkinetic movement disorders," Pipeline Projects Session, 11th annual meeting of American Society for Experimental NeuroTherapeutics, Arlington, VA, 2009, 9 slides.
Marder et al., "Kinect 3: a randomized, double-blind, placebo-controlled phase 3 trial of valbenazine (NBI-98854) for Tardive Dyskinesia," American Academy of Neurology, 2016, 9 pages.
Margolese et al., "Tardive dyskinesia in the era of typical and atypical antipsychotics. Part 1: pathophysiology and mechanisms of induction," Can J Psychiatry, Aug. 2005, 50(9):541-47.
Material Safety Data Sheet. Product Name Valbenazine tosylate. Published May 1, 2014 (see Revision date). Retrieved from internet May 23, 2020. URL: https://www.selleckchem.com/msds/MSDS_S9500.pdf.
McBride et al., "Using Drosophila as a tool to identify Pharmacological Therapies for Fragile X Syndrome," Drug Discov Today Technol., Sep. 24, 2012, 10(1):e129-e136.
Mehvar et al., "Pharmacokinetics of tetrabenazine and its major metabolite in man and rat. Bioavailability and dose dependency studies," Drug Metabolism and Distribution, 1987, 15(2):250-255.
mentalhealthamerica.net [online], "Depression," [retrieved on Dec. 17, 2018], retrieved from URL<http://www.mentalhealthamerica.net/conditions/depression>, 3 pages.
Mineur et al., "Social behavior deficits in the Fmr1 mutant mouse," Behav Breain Res., Mar. 15, 2006, 168(1):172-175.
Muller et al., "Valbenazine for the treatment of tardive dyskinesia," Expert Review of Neurotherapeutics, 2017, 17(2):1135-1144.
Near, "[3H]Dihydrotetrabenazine binding to bovine striatal synaptic vesicles," Mol. Pharmacol., Sep. 1986, 30:252-257.

Nikoloff et al., "Association between CYP2D6 genotype and tardive dyskinesia in Korean schizoprenics," The Pharmacogenomics J, 2002, 2:400-407.
ninds.nih.gov [online], Available on or before Jan. 24, 2013, via Internet Archive: Wayback Machine URL <https://web.archive.org/web/20130124115120/www.ninds.nih.gov/disorders/rett/detail_rett.htm>, retrieved on Dec. 17, 2018], retrieved from URL<www.ninds.nih.gov/disorders/rett/detail_rett.htm>, 6 pages.
Nunes et al., "Effort-related motivational effects of the VMAT-2 inhibitor tetrabenazine: implications for animal models of the motivational symptoms of depression," J. Neurosci., 2013, 33(49):19120-30.
Nyhan et al., "Lesch-Nyhan Syndrome," Posted Sep. 25, 2000[last update May 15, 2014], 21 pages.
O'Brien et al., "NBI-98854, a selective monoamine transport inhibitor for the treatment of tardive dyskinesia: a randomized, double-blind, placebo-controlled study," Movement Disorders, 2015, 30(12):1681-1687.
Ondo et al, "Tetrabenazine treatment for tardive dyskinesia: assessment by randomized videotape protocol," Am J Psychiatry, Aug. 1999, 156(8):1279-1281.
Owesson-White et al., "Sources contributing to the average extracellular concentration of dopamine in the nucleus accumbens," J Neurochem., 2012, 121:252-62.
Pallanti and Quercioli, "Treatment-refractory obsessive-compulsive disorder: methodological issues, operational definitions and therapeutic lines," Neuropsychopharmacol. Biol Psychiatry, May 2006, 30(3):400-412.
PCT International Preliminary Report on Patentability in International Appln. No. PCT/US2018/051579, dated Apr. 2, 2020, 25 pages.
PCT International Search Report and Written Opinion in International Appln. No. PCT/US2018/051579, dated Mar. 18, 2019, 36 pages.
Piccinni et al., "Effectiveness of a Clozapine-Aripiprazole Combination in Tourette Syndrome and Bipolar Spectrum Disorder," J Neuropsychiatry Clin Neurosci., Jan. 1, 2013, 25:1.
Pincus, "Management of digoxin toxicity," Aust. Prescr., 2016, 39(1):18-21.
Pittenger et al., "Pharmacological treatment of obsessive-compulsive disorder," Psychiatr. Clin. North Am., 2014, 37(3):375-391.
Poliak et al., "Juxtaparanodal clustering of Shaker-like K+ channels in myelinated axons depends on Caspr2 and TAG-1," J Cell Biol., Sep. 15, 2003, 162(6):1149-1160.
Porta et al., "Tourette's syndrome and role of tetrabenazine," Clin Drug Invest., 2008, 28(7):443-459.
Portman et al., "Behavioral abnormalities and circuit defects in the basal ganglia of a mouse model of 16p11.2 deletion syndrome," Cell Rep., May 22, 2014, 7(4):1077-1092.
Prescott, "Powder handling," Pharmaceutical Process Scale-Up, Jan. 2011, 195-209.
Provenzano et al., "Mutant mouse models of autism spectrum disorders," Dis. Markers, 2012, 33(5):225-239.
Rao et al, "Review article: metoclopramide and tardive dyskinesia," Aliment Pharmacol Ther 2010, 31(1):11-19.
Remington et al., "Tetrabenazine Augmentation in Treatment-Resistant Schizophrenia," Journal of Clinical Psychopharmacology, Feb. 1, 2012, 32(1):95-99.
Robey et al., "Modes and patterns of self-mutilation in persons with Lesch-Nyhan disease," Dev Med Child Neurol. Mar. 2003, 45(3):167-171.
Russian Office Action in Russian Application No. 2016147523, dated Dec. 27, 2018, 18 pages.
Santus and Baker, "Osmotic drug delivery: a review of the patent literature," J. Controlled Release, 1995, 35(1)1-21.
Sawant, "Necessity of Establishing Chemical Integrity of Polymorphs of Drug Substance Using a Combination of NMR, HPLC, Elemental Analysis, and Solid-State Characterization Techniques: Case Studies," Organic Process Research & Development 17.3, 2013, :519-532.

(56) References Cited

OTHER PUBLICATIONS

Scherman et al., "[3H]dihydrotetrabenazine, a new in vitro monoaminergic probe for human brain," Journal of Neurochemistry 1988, 50(4):1131-1136.
Schneider et al., "Efficacy and adverse effects of atypical antipsychotics for dementia: meta-analysis of randomized, placebo-controlled trials," Am J Geritr Psychiatry., 2006, 14(3):191-210.
Schretlen et al., "Behavioral aspects of Lesch-Nyhan disease and its variants," Dev Med Child Neurol., Oct. 2005, 47(10):673-677.
Schretlen et al., "Neurocognitive functioning in Lesch-Nyhan disease and partial hypoxanthine-guanine phosphoribosyltransferase deficiency," J Int. Neuropsychol Soc., 2001, 7:805-812.
Scott et al., Making and Breaking Serotonin Neurons and Autism, Int J Devl Neuroscience., 2005, 23:277-285.
Sever et al., "Process Analytical Technology in Solid Dosage Development and Manufacturing," Developing Solid Oral Dosage Forms Pharmaceutical Theory and Practice, Jan. 2008, 827-841.
Shen et al. "Safety and Efficacy of Tetrabenazine and use of Cocomitant Medications during Long-Term, Open-Label Treatment of Chorea Associated with Huntington's and Other Diseases," Tremor and Other Myperkinetic Movements, Oct. 22, 2013, https://tremorjournal.org/index.php/tremor/article/view/191, pp. 1-12.
Siegert et al., "Efficacy and Safety of Valbenazine (NBI-98854) in Subjects with Tardive Dyskinesia: Results of a Long-Term Study (KINECT 3 Extension)," Poster Presented At The Xxii World Congress On Parkinson's Disease And Related Disorders, Nov. 12-15, 2017, 1 page.
Silverman et al., "Behavioural phenotyping assays for mouse models of autism," Nature Reviews Neuroscience, Jul. 2010, 11(7):490-502.
Simpson et al., "A rating scale for extrapyramidal side effects," Acta Psychiatry Scand Suppl, 1970, 212:11-19.
Singer et al., "Assessing the Effectiveness of Valbenazine in the Treatment of Tardive Dyskinesia as Determined by the AIMS and PGIC: Results from the KINECT 4 Trial," Poster Presented At The 22nd Annual International Congress Of Parkinson's Disease And Movement Disorders, Oct. 5-9, 2018, 1 page.
Skor et al., "Differences in dihydrotetrabenazine isomer concentrations following administration of tetrabenazine and valbenazine," Drugs R D, 2017, 17:449-459.
Smolders et al., "Pharmacokinetics, efficacy, and safety of Hepatitis C virus drugs in patients with liver and/or renal impairment," Drug safety, 2016, 39(7):589-611.
Solon, "Risperidone-reserpine combination in refractory psychosis," Schizophrenia Research, Dec. 1, 1996, 22(3):265-266.
Spencer et al., "Social behavior in Fmr1 knockout mice carrying a human FMR1 transgene," Behave Neurosci., Jun. 2008, 122(3):710-715.
Spina et al., "Effect of fluoxetine on the plasma concentrations of clozapine and its major metabolites in patients with schizophrenia," International Clinical Psychopharmacology, May 1, 1998, 13(3):141-145.
STN CAS RN: 1639208-54-0, entered STN Dec. 22, 2014, 1 page.
Sun et al., "Preparation and evaluation of tetrabenazine enantiomers and all eight stereoisomers of dihydrotetrabenazine as VMAT2 inhibitors," Eur. J. Med. Chem., 2011, 46(5):1841-1848.
Table 14.3.5.14.1, "Young Mania Rating Scale (YMRS) Total Score and Change from Baseline (CFB) Values by Visit and Treatment Group," Neurocrine Biosciences, Inc., Oct. 8, 2015, 6 pages.
Tandon et al., "World Psychiatric Association Pharmacopsychiatry Section Statement on Comparative Effectiveness of Antipsychotics in the Treatment of Schizophrenia," Schizophrenia Research, Mar. 1, 2008, 100(1-3):20-38.
Tarsy and Baldessarini, "Epidemiology of tardive dyskinesia: is risk declining with modern antipsychotics?" Movement Disorders, May 2006, 21(5):589-598.
Tauber et al., "Elevated Levels of the Vesicular Monoamine Transporter and a Novel Repetitive Behavior in the *Drosophila* Model of Fragile X Syndrome," PLOS ONE, Nov. 2, 2011, 6(11):e27100.
Teasdale et al., "Mechanism and Processing Parameters Affecting the Formation of Methyl Methanesulfonate from Methanol and Methanesulfonic Acid: An Illustrative Example for Sulfonate Ester Impurity Formation," Org Process Res. Dev., 2009, 15:13429-433.
Teasdale, "Sulfonate Esters—How Real is the Risk? Summary of Key Findings from PQRI Studies of the Reaction Between Sulfonic acids and Alcohols," 2007, 42 pages.
Teasdale, "Sulphonate esters: a real or imagined risk? PQRI studies to determine actual risk," British Pharmaceutical Conference, Manchester Sep. 10-12, 2007, J Pharmacy Pharmacol. A-78, Abstract 218.
Tenback et al, "Incidence and persistence of tardive dyskinesia and extrapyramidal symptoms in schizophrenia," J Psychopharmacol, Jul. 2010, 24(7):1031-1035.
Teng et al., "Lobeline displaces [3H]dihydrotetrabenazine binding and releases [3H]dopamine from rat striatal synaptic vesicles: comparison with d-amphetamine," J Neurochem. 1998, 71(1):258-265.
Thai-Curato et al., "Cardiovascular profile of valbenazine: analysis of pooled dated from three randomized, double-blind, placebo-controlled trials," Drug Safety, 2017, 41(4):429-440.
Tian et al., "CYP3A4-mediated pharmacokinetic interactions in cancer therapy," Curr. Drug Metab., 2014, 15(8):808-17.
Tomemori et al., "A gene-targeted mouse model for chorea-acanthocytosis," J Neurochem, 2005, 92(4):759-766.
Traynor, "Valbenazine approved for treatment of tardive dyskinesia," ASHP, Apr. 17, 2017, retrieved from URL: https://www.ashp.org/news/2017/04/17/valbenazine-approved-for-treatment-of-tardive-dyskinesia?loginreturnUrl=SSOCheckOnly, retrieved on Jun. 22, 2020, 3 pages.
Tsoussis et al., "Disclosure of cancer diagnosis: the Greek experience," JBUON, Open Access Journal aimed at the rapid diffusion of scientific knowledge in Oncology, 2013, 18(2):516-526.
United States Pharmacopoeia ("USP"), "Bulk Density and Tapped Density of Powders," <616>, 2015, 3 pages.
United States Pharmacopoeia ("USP"), "Disintegration," <701>, 2016, 4 pages.
United States Pharmacopoeia ("USP"), "Dissolution," <711>, 2011, 8 pages.
United States Pharmacopoeia ("USP"), "Uniformity of Dosage Units," <905>, 2016, 9 pages.
United States Pharmacopoeia, "Light Diffraction Measurement of Particle Size," <429>, 2016, 8 pages.
US Department of Health and Human Services, and Food and Drug Administration, "Size, Shape, and Other Physical Attributes of Generic Tablets and Capsules," Jun. 2015, 10 pages.
Verkerk et all., "Identification of a gene (FMR-1) containing a CGG repeat coincident with a breakpoint cluster region exhibiting length variation in fragile X syndrome," Cell, May 1991, 65(5):905-914.
Verma et al., "Formulation aspects in the development of osmotically controlled oral drug delivery systems," J. Controlled Release, Feb. 19, 2002, 79(1-3):7-27.
Verma et al., "Osmotically controlled oral drug delivery," Drug Development and Industrial Pharmacy, Jul. 2000, 26(7):695-708.
Watts et al., "Clinical and biochemical studioes on treatment of Lesch-Nylan Syndrome," Archives of Disease in Childhood., 1974, 49:693-702.
Weihe and Eiden, "Chemical neuroanatomy of the vesicular amine transporters.," The FASEB Journal, Dec. 2000, 14(15):2435-2449.
Woods et al, "Incidence of tardive dyskinesia with atypical versus conventional antipsychotic medications: a prospective cohort study," J Clin Psychiatry, Apr. 2010, 71(4):463-474.
Yamashita et al., "Modeling of rifampicin-induced CYP3A4 activation dynamics for the prediction of clinical drug-drug interactions in vitro data," PLoS One, 2013, 8(9):e70330, 11 pages.
Yasumoto et al., "Inhibitory effect of selective serotonin reuptake inhibitors on the vesicular monoamine transporter 2," Neuroscience Letters, May 1, 2009, 454(3):229-232.
Zhang et al, "Synergistic Effects of Olanzapine and other Antipsychotic Agents in Combination with Fluoxetine on Norepinephrine and Dopamine release in rate Prefrontal Cortex," Neuropsychopharmacology, Sep. 1, 2000, 23(3):250-262.

SYNTHETIC METHODS FOR PREPARATION OF (S)-(2R,3R,11BR)-3-ISOBUTYL-9,10-DIMETHOXY-2,3,4,6,7,11B-HEXAHYDRO-1H-PYRIDO[2,1,-A]ISOQUINOLIN-2-YL 2-AMINO-3-METHYLBUTANOATE DI(4-METHYLBENZENESULFONATE)

CROSS REFERENCE TO RELATED APPLICATION

This application is a continuation of U.S. application Ser. No. 16/509,552, filed on Jul. 12, 2019, which is a continuation of U.S. application Ser. No. 16/196,234, filed Nov. 20, 2018, which is a continuation of U.S. application Ser. No. 15/388,960, filed Dec. 22, 2016, now issued U.S. Pat. No. 10,160,757, which claims the benefit of U.S. Provisional Application No. 62/387,442 filed Dec. 23, 2015. The disclosure of each of these priority documents which is incorporated herein by reference in its entirety.

FIELD

Provided herein are processes for the preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable solvate, hydrate, or polymorph thereof.

BACKGROUND

Hyperkinetic disorders are characterized by excessive, abnormal involuntary movement. These neurologic disorders include tremor, dystonia, ballism, tics, akathisia, stereotypies, chorea, myoclonus and athetosis. Though the pathophysiology of these movement disorders is poorly understood, it is thought that dysregulation of neurotransmitters in the basal ganglia plays an important role. (Kenney et. al., *Expert Review Neurotherapeitics*, 2005, 6, 7-17). The chronic use and high dosing of typical neuropletics or centrally acting dopamine receptor blocking antiemetics predispose patients to the onset of tardive syndromes. Tardive dyskinesia, one subtype of the latter syndromes, is characterized by rapid, repetitive, stereotypic, involuntary movements of the face, limbs, or trunk. (Muller, *Expert Opin. Investig. Drugs*, 2015, 24, 737-742).

The reversible inhibition of the vesicular monoamine transporter-2 system (VMAT2) by 3-isobutyl-9,10-dimethoxy-1,3,4,6,7,11b-hexahydro-2H-pyrido[2,1-a]isoquinolin-2-one, also known as tetrabenazine (TBZ), improves the treatment of various hyperkinetic movement disorders. However, the drawbacks to such treatment are the fluctuating response, the need for frequent intake due to TBZ rapid metabolism, and side effects. Side effects associated with TBZ include sedation, depression, akathisia, and parkinsonism.

TBZ, which contains two chiral centers and is a racemic mix of two stereoisomers, is rapidly and extensively metabolized in vivo to its reduced form, 3-isobutyl-9,10-dimethoxy-1,3,4,6,7,11b-hexahydro-2H-pyrido[2,1-a]isoquinolin-2-ol, also known as dihydrotetrabenazine (DHTBZ). DHTBZ is thought to exist as four individual isomers: (±) alpha-DHTBZ and (±) beta-DHTBZ. The (2R,3R,11bR) or (+) alpha-DHTBZ is believed to be the absolute configuration of the active metabolite (Kilbourn et al., *Chirality*, 1997, 9, 59-62). Tetrabenazine has orphan drug status in US and is approved in certain European countries. Its use is also allowed for therapy of chorea in patients with Hungtington's disease. However, tetrabenazine is rapidly metabolized and must frequently be administered throughout the day. (Muller, *Expert Opin. Investig. Drugs*, 2015, 24, 737-742). Therefore, there is an unmet need in the art to develop effective therapeutics for treatment of hyperkinetic movement disorders, including tardive dyskinesia.

Valbenazine, (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester, the prodrug of the (+)-α-isomer of dihydrotetrabenazine, recently showed a distinctive improvement in the treatment of hyperkinetic movement disorders, including tardive dyskinesia symptoms, with improved pharmacokinetic and tolerability profiles.

A method for synthesizing (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester has been described in U.S. Pat. Nos. 8,039,627 and 8,357,697, the disclosure of each of which is incorporated herein by reference in its entirety.

SUMMARY OF THE DISCLOSURE

Provided herein are safe, efficient, cost effective, and/or readily scalable methods for the preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) or a pharmaceutically acceptable solvate, hydrate, or polymorph thereof. In other embodiments, the methods provide (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) of greater than 95% purity.

Methods provided herein are generally directed to: (a) reacting (2R,3R,11bR)-3-isobutyl-9,10-dimethoxy-2,3,4,6,7,11b-hexahydro-1H-pyrido[2,1-a]isoquinolin-2-ol or a salt thereof with a suitably protected L-valine under conditions suitable to form (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate; (b) deprotecting (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate to form (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride, or a pharmaceutically acceptable solvate, hydrate, or polymorph thereof; and (c) converting (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride to (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) or a pharmaceutically acceptable solvate, hydrate, or polymorph thereof.

DETAILED DESCRIPTION OF THE INVENTION

Unless defined otherwise, all technical and scientific terms used herein have the same meaning as those commonly understood by one of ordinary skill in the art. All publications and patents referred to herein are incorporated by reference herein in their entireties.

Definitions

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "alkyl" refers to a linear or branched saturated monovalent hydrocarbon radical, wherein the alkyl is optionally substituted with one or more substituents Q as described herein elsewhere. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "alkenyl" refers to a linear or branched monovalent hydrocarbon radical, which contains one or more, in one embodiment, one to five, in another embodiment, one, carbon-carbon double bond(s), wherein the alkenyl is optionally substituted with one or more substituents Q as described herein elsewhere. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one to five, in another embodiment, one, carbon-carbon triple bond(s), wherein the alkynyl is optionally substituted with one or more substituents Q as described herein elsewhere. For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH), propynyl (including all isomeric forms, e.g., 1-propynyl (—C≡CCH$_3$) and propargyl (—CH$_2$C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "cycloalkyl" refers to a cyclic monovalent hydrocarbon radical, wherein the cycloalkyl is optionally substituted with one or more substituents Q as described herein elsewhere. In one embodiment, cycloalkyl groups may be saturated or unsaturated but non-aromatic, and/or spiro, and/or non-spiro, and/or bridged, and/or non-bridged, and/or fused bicyclic groups. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl.

The term "aryl" refers to a monovalent monocyclic aromatic group and/or monovalent polycyclic aromatic group that contain at least one aromatic carbon ring, wherein the aryl is optionally substituted with one or more substituents Q as described herein elsewhere. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. The term "aryl" also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl).

The term "aralkyl" or "arylalkyl" refers to a monovalent alkyl group substituted with one or more aryl groups, wherein the aralkyl or arylalkyl is optionally substituted with one or more substituents Q as described herein elsewhere. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl.

The term "heteroaryl" refers to a monovalent monocyclic aromatic group and/or monovalent polycyclic aromatic group that contain at least one aromatic ring, wherein at least one aromatic ring contains one or more heteroatoms independently selected from O, S, N, and P in the ring. Heteroaryl groups are bonded to the rest of a molecule through the aromatic ring. Each ring of a heteroaryl group can contain one or two O atoms, one or two S atoms, one to four N atoms, and/or one or two P atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents Q as described herein elsewhere.

The term "heterocyclyl" or "heterocyclic" refers to a monovalent monocyclic non-aromatic ring system and/or monovalent polycyclic ring system that contain at least one non-aromatic ring, wherein one or more of the non-aromatic ring atoms are heteroatoms independently selected from O, S, N, and P; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of a molecule through the non-aromatic ring. In certain embodiments, the heterocyclyl is a monocyclic, bicyclic, tricyclic, or tetracyclic ring system, which may be spiro, fused, or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, 13-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl is optionally substituted with one or more substituents Q as described herein elsewhere.

The term "alkene" refers to a linear or branched hydrocarbon, which contains one or more, in one embodiment, one to five, in another embodiment, one, carbon-carbon double bond(s), wherein the alkene is optionally substituted with one or more substituents Q as described herein elsewhere. The term "alkene" embraces a compound having a "cis" or "trans" configuration or a mixture thereof, or alternatively, a "Z" or "E" configuration or a mixture thereof, as appreciated by those of ordinary skill in the art. For example, $C_{2-6}$ alkene refers to a linear unsaturated hydrocarbon of 2 to 6 carbon atoms or a branched unsaturated hydrocarbon of 3 to 6 carbon atoms. In certain embodiments, the alkene is a linear hydrocarbon of 2 to 20 ($C_{2-20}$), 2 to 15 ($C_{2-15}$), 2 to 10 ($C_{2-10}$), or 2 to 6 ($C_{2-6}$) carbon atoms, or a branched hydrocarbon of 3 to 20 ($C_{3-20}$), 3 to 15 ($C_{3-15}$), 3 to 10 ($C_{3-10}$), or 3 to 6 ($C_{3-6}$) carbon atoms.

The term "cycloalkene" refers to a cyclic hydrocarbon, which contains one or more, in one embodiment, one to five, in another embodiment, one, carbon-carbon double bond(s), wherein the cycloalkene is optionally substituted with one or more substituents Q as described herein elsewhere. In one embodiment, the cycloalkene may be non-aromatic, and/or spiro, and/or non-spiro, and/or bridged, and/or non-bridged, and/or fused bicyclic. In certain embodiments, the cycloalkene has from 3 to 20 ($C_{3-20}$), from 3 to 15 ($C_{3-15}$), from 3 to 10 ($C_{3-10}$), or from 3 to 7 ($C_{3-7}$) carbon atoms.

The term "arene" refers to a monocyclic aromatic compound and/or polycyclic aromatic compound that contain at least one aromatic carbon ring, wherein the arene is optionally substituted with one or more substituents Q as described herein elsewhere. In certain embodiments, the arene has from 6 to 20 ($C_{6-20}$), from 6 to 15 ($C_{6-15}$), or from 6 to 10 ($C_{6-10}$) ring atoms. The term "arene" also refers to bicyclic or tricyclic carbon rings, where one of the rings is aromatic and the other(s) may be saturated, partially unsaturated, or aromatic.

The term "heteroarene" refers to a monocyclic aromatic and/or polycyclic aromatic compound that contain at least one aromatic ring, wherein at least one aromatic ring contains one or more heteroatoms independently selected from O, S, N, and P in the ring. Each ring of a heteroarene can contain one or two O atoms, one or two S atoms, one to four N atoms, and/or one or two P atoms, provided that the total number of heteroatoms in each ring is four or less and each ring contains at least one carbon atom. In certain embodiments, the heteroarene has from 5 to 20, from 5 to 15, or from 5 to 10 ring atoms. In certain embodiments, the heteroarene is optionally substituted with one or more substituents Q as described herein elsewhere.

The term "heterocycle" refers to a monocyclic non-aromatic ring system and/or non-aromatic polycyclic ring system, wherein one or more of the non-aromatic ring atoms are heteroatoms, each of which is independently selected from O, S, N, and P: and the remaining ring atoms are carbon atoms. In certain embodiments, the heterocycle has from 3 to 20, from 3 to 15, from 3 to 10, from 3 to 8, from 4 to 7, or from 5 to 6 ring atoms. In certain embodiments, the heterocycle is a monocyclic, bicyclic, tricyclic, or tetracyclic ring system, which may be spiro, fused, or bridged, and in which nitrogen or sulfur atoms may be optionally oxidized, nitrogen atoms may be optionally quaternized, and some rings may be partially or fully saturated. In certain embodiments, the heterocycle is optionally substituted with one or more substituents Q as described herein elsewhere.

The term "alcohol" refers to alkyl-OH, alkenyl-OH, alkynyl-OH, cycloalkyl-OH, aryl-OH, aralkyl-OH, heteroaryl-OH, or heterocyclyl-OH, wherein the alkyl, alkenyl, alkynyl, cycloalkyl, aryl, aralkyl, heteroaryl, and heterocyclyl are each as defined herein.

The term "carboxylic acid" refers to alkyl-COOH, alkenyl-COOH, alkynyl-COOH, cycloalkyl-COOH, aryl-COOH, aralkyl-COOH, heteroaryl-COOH, or heterocyclyl-COOH, wherein the alkyl, alkenyl, alkynyl, cycloalkyl, aryl, aralkyl, heteroaryl, and heterocyclyl are each as defined herein.

The term "carboxylic acid ester" or "ester" refers to alkyl-COOR', alkenyl-COOR', alkynyl-COOR', cycloalkyl-COOR', aryl-COOR', aralkyl-COOR', heteroarylCOOR', or heterocyclyl-COOR', and each R' is independently wherein alkyl, alkenyl, alkynyl, cycloalkyl, aryl, aralkyl, heteroaryl, and heterocyclyl; and wherein each alkyl, alkenyl, alkynyl, cycloalkyl, aryl, aralkyl, heteroaryl, and heterocyclyl is as defined herein.

The term "optionally substituted" is intended to mean that a group or substituent, such as an alkyl, alkenyl, alkynyl, cycloalkyl, aryl, aralkyl, heteroaryl, or heterocyclyl group, may be substituted with one or more substituents Q, each of which is independently selected from, e.g., (a) oxo (═O), halo, cyano (—CN), and nitro (—NO₂); (b) $C_{1-6}$ alkyl, $C_{2-6}$ alkenyl, $C_{2-6}$ alkynyl, $C_{3-10}$ cycloalkyl, $C_{6-14}$ aryl, $C_{1-15}$ aralkyl, heteroaryl, and heterocyclyl, each of which is further optionally substituted with one or more, in one embodiment, one, two, three, or four, substituents Q; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NRa)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$N$^b$R$^c$, —P(O)R$^a$R$^d$, —P(O)(OR$^a$)R$^d$, P(O)(OR$^a$)(OR$^d$), —SR$^a$—S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl, each of which is optionally substituted with one or more, in one embodiment, one, two, three, or four, substituents Q$^a$; or (iii) R$^b$ and R$^c$ together with the N atom to which they are attached form heteroaryl or heterocyclyl, each of which optionally substituted with one or more, in one embodiment, one, two, three, or four, substituents Q$^a$. As used herein, all groups that can be substituted are "optionally substituted," unless otherwise specified.

The term "isotopically enriched" refers to an atom having an isotopic composition other than the natural isotopic composition of that atom. "Isotopically enriched" may also refer to a compound containing at least one atom having an isotopic composition other than the natural isotopic composition of that atom.

With regard to the compounds provided herein, when a particular atomic position is designated as having deuterium or "D," it is understood that the abundance of deuterium at that position is substantially greater than the natural abundance of deuterium, which is about 0.015%. A position designated as having deuterium typically has a minimum isotopic enrichment factor of, in particular embodiments, at least 1000 (15% deuterium incorporation), at least 2000 (30% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium position.

The isotopic enrichment of the compounds provided herein can be determined using conventional analytical methods known to one of ordinary skill in the art, including mass spectrometry, nuclear magnetic resonance spectroscopy, and crystallography.

Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., *Food Cosmet. Toxicol.*, 20: 393 (1982); Lijinsky et. al., *J. Nat. Cancer Inst.*, 69: 1127 (1982); Mangold et. al., *Mutation Res.* 308: 33 (1994); Gordon et. al., *Drug Metab. Dispos.*, 15: 589 (1987); Zello et. al., *Metabolism*, 43: 487 (1994); Gately et. al., *J. Nucl. Med.*, 27: 388 (1986); Wade D, *Chem. Biol. Interact.* 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g., Foster et al., *Adv. Drug Res.*, vol. 14, pp. 1-36 (1985); Kushner et al., *Can. J. Physiol. Pharmacol.*, vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as T$_2$O. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}$C or $^{14}$C for carbon, $^{33}$S, $^{34}$S, or $^{36}$S for sulfur, $^{15}$N for nitrogen, and $^{17}$O or $^{18}$O for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein may produce a detectable KIE that will affect the pharmacokinetic, pharmacologic, and/or toxicological profiles of a compound provided herein in comparison with a similar compound having a natural isotopic composition.

The term "isotopic variant" refers to a therapeutic agent that contains an unnatural proportion of an isotope at one or more of the atoms that constitute such a therapeutic agent. In certain embodiments, an "isotopic variant" of a therapeutic agent contains unnatural proportions of one or more isotopes, including, but not limited to, hydrogen (H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine 123 ($^{123}$I), iodine-125 ($^{125}$I), iodine-127 ($^{127}$I), iodine-129 ($^{129}$I), and iodine-131 ($^{131}$I). In certain embodiments, an "isotopic variant" of a therapeutic agent contains unnatural proportions of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine 123 ($^{123}$I), iodine-125 ($^{125}$I), iodine-127 ($^{127}$I), iodine-129 ($^{129}$I), and iodine-131 ($^{131}$I).

It will be understood that, in a therapeutic agent, any hydrogen can be $^2$H, for example, or any carbon can be $^{13}$C, for example, or any nitrogen can be $^{15}$N, for example, or any oxygen can be $^{18}$O, for example, where feasible according to the judgment of one of skill. In certain embodiments, an "isotopic variant" of a therapeutic agent contains unnatural proportions of deuterium (D).

As used in the specification and the accompanying claims, the indefinite articles "a" and "an" and the definite article "the" include plural as well as singular referents, unless the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 300%, 25%, 20%, 15%, 10%, 9%, 8%, 7%, 6%, 5%, 4%, 3%, 2%, 1%, 0.5%, or 0.05% of a given value or range. In certain embodiments, "about" or "approximately" with reference to temperature means within 0.5° C.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The term "crystalline form" of a compound can refer to any crystalline form of the compound as a free acid, the compound as a free base, as an acid addition salt of the compound, an base addition salt of the compound, a complex of the compound, a solvate (including hydrate) of the compound, or a co-crystal of the compound. The term "solid form" of a compound can refer to any crystalline form of the compound or any amorphous form of the compound as a free acid, the compound as a free base, as an acid addition salt of the compound, an base addition salt of the compound, a complex of the compound, or a solvate (including hydrate) of the compound, or a co-precipitation of the compound. In many instances, the terms "crystalline form" and "solid form" can refer to those that are pharmaceutically acceptable, including, for example, those of pharmaceutically acceptable addition salts, pharmaceutically acceptable complexes, pharmaceutically acceptable solvates, pharmaceutically acceptable co-crystals, and pharmaceutically acceptable co-precipitations.

The term "hyperkinetic disorder" or "hyperkinetic movement disorder" or "hyperkinesias" refers to disorders or diseases characterized by excessive, abnormal, involuntary movements. These neurologic disorders include but are not limited to tremor, dystonia, ballism, tics, akathisia, stereotypies, chorea, myoclonus and athetosis.

The term "VMAT2" refers to human monoamine transporter isoform 2, an integral membrane protein that acts to transport monoamines, particularly neurotransmitters such as dopamine, norepinephrine, serotonin, and histamine, from cellular cytosol into synaptic vesicles.

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia, or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example only and without limitation, sodium, potassium, calcium, magnesium, ammonium, tetraalkylammonium, and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

The term "amino acid" refers to naturally occurring and synthetic α, β, γ, or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In one embodiment, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl, or β-histidinyl.

The term "substantially free" when referring to a composition that is "substantially free" of a compound means that the composition contains no greater than about 20% by weight, no greater than about 10% by weight, no greater than about 5% by weight, no greater than about 3% by weight, no greater than about 1% by weight, no greater than about 0.5% by weight, no greater than about 0.2% by weight, no greater than about 0.1% by weight, no greater than about 0.01% by weight, no greater than about 0.001% by weight, or no greater than about 0.0001% by weight of the compound.

The term "substantially pure" when referring to a compound or composition means that the compound or composition has a purity of no less than about 80% by weight, no less than about 90% by weight, no less than about 95% by weight, no less than about 96% by weight, no less than about 97% by weight, no less than about 98% by weight, no less than about 99% by weight, no less than about 99.5% by weight, no less than about 99.9% by weight, no less than about 99.95% by weight, no less than about 99.99% by weight, g no less than about 99.995% by weight, no less than about 99.999% by weight, no less than about 99.9995% by weight, or no less than about 99.9999% by weight.

The terms "process" and "method" are used interchangeably to refer to a method disclosed herein for a compound preparation. Modifications to the processes and methods disclosed herein (e.g., starting materials, reagents, protecting groups, solvents, temperatures, reaction times, and/or purification) that are well known to those of ordinary skill in the art are also encompassed by the disclosure.

The terms "adding" "reacting" and "mixing" are used interchangeably to refer to contacting one reactant, reagent, solvent, catalyst, or a reactive group with another reactant, reagent, solvent, catalyst, or reactive group. Unless otherwise specified, reactants, reagents, solvents, catalysts, and reactive groups can be added individually, simultaneously, or separately, and/or can be added in any order. They can be added in the presence or absence of heat, and can optionally be added under an inert atmosphere (e.g., $N_2$ or Ar). In certain embodiments, the term "reacting" can also refer to in situ formation or intra-molecular reaction where the reactive groups are in the same molecule.

The term "substantially complete" when referring to a reaction means that the reaction contains no greater than about 50%, no greater than about 40%, no greater than about 30%, no greater than about 20%, no greater than about 10%, no greater than about 5%, no greater than about 4%, no greater than about 3%, no greater than about 2%, no greater than about 1%, no greater than about 0.5%, no greater than about 0.1%, or no greater than about 0.05% of a starting material left.

If the stereochemistry of a structure or a portion thereof is not indicated, e.g., with bold or dashed lines, the structure or portion thereof is to be interpreted as encompassing all stereoisomers of the structure.

The phrase "a pharmaceutically acceptable salt, solvate, hydrate, or polymorph thereof" has the same meaning as the phrase "a pharmaceutically acceptable salt, solvate, hydrate, or polymorph of the compound referenced therein; or a pharmaceutically acceptable salt, solvate, hydrate, or polymorph of an enantiomer or a mixture of enantiomers of the compound referenced therein."

Processes

Provided herein are methods for the preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable solvate, hydrate, or polymorph thereof, with at least about 95% purity. In certain embodiments, the methods provided herein are safe, efficient, cost effective, and/or readily scalable. In certain embodiments, the methods provided herein are suitable for the large scale or commercial production of(S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable solvate, hydrate, or polymorph thereof.

In one embodiment, provided herein is a method for preparing (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable solvate, hydrate, or polymorph thereof, with at least about 95% purity; comprising converting (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride to (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable solvate, hydrate, or polymorph thereof.

In one embodiment, the step of converting (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride to (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) comprises: (a) reacting (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride with a base and (b) reacting the product of (a) with p-toluenesulfonic acid.

In another embodiment, (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride is contacted with a base in a first solvent.

In certain embodiments, the base comprises an inorganic base. In some embodiments, the bases comprises a carbonate base. In some embodiments, the base comprises sodium carbonate, sodium hydrogen carbonate, potassium carbonate, or potassium hydrogen carbonate. In some embodiments, the base is sodium hydrogen carbonate.

In some embodiments, the solvent in step (a) (i.e., reacting (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride with a base) is a hydrocarbon, chlorinated hydrocarbon, alcohol, ether, ester, carbonate, amide, nitrile, sulfoxide, sulfone, nitro compound, heteroarene, heterocycle, water, or a mixture thereof. In certain embodiments, the solvent is a chlorinated hydrocarbon. In yet other embodiments, the solvent is dichloromethane.

In certain embodiments, the reaction of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride with a base is performed at a temperature ranging from about 0 to about 30° C., from about 5 to about 25° C., from about 5 to about 20° C. In some embodiments, the reaction is performed at a temperature ranging from about 20 to about 30° C. In yet other embodiments, the reaction is performed at a temperature of about 25° C.

In another embodiment, the reaction of the product of (a) with p-toluensufonic acid, is conducted in a second solvent.

In some embodiments, the solvent is an hydrocarbon, chlorinated hydrocarbon, alcohol, ether, ketone, ester, carbonate, amide, nitrile, sulfoxide, sulfone, nitro compound, heteroarene, heterocycle, carboxylic acid, phosphoramide, carbon sulfide, water, or a mixture thereof.

In certain embodiments, the solvent is petroleum ether, pentane, hexane(s), heptane, octane, isooctane, cyclopentane, cyclohexane, methylcyclohexane, benzene, toluene, xylene, tetralin, cumene, dichloromethane (DCM), 1,2-dichloroethane, 1,1-dichloroethene, 1,2-dichloroethene, chloroform, trichloroethane, trichloroethene, carbon tetrachloride, chlorobenzene, trifluoromethylbenzene, methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, ethyleneglycol, diethyl ether, diisopropyl ether, methyl t-butyl ether (MTBE), diphenyl ether, 1,2-dimethoxyethane, bi(2-methoxyethyl)ether, 1,1-dimethoxymethane, 2,2-dimethoxypropane, anisole, acetone, butanone, methyl ethyl ketone (MEK), methyl isopropyl ketone, methyl butyl ketone, methyl isobutyl ketone (MIBK), methyl acetate, ethyl formate, ethyl acetate, propyl acetate, isopropyl acetate, isobutyl acetate, butyl acetate, ethylene carbonate, propylene carbonate, formamide, N,N-dimethylformamide (DMF), N,N-dimethylacetamide, acetonitrile (ACN), dimethyl sulfoxide (DMSO), sulfolane, nitromethane, nitrobenzene, N-methyl pyrrolindone, 2-methyl tetrahydrofuran, tetrahydrofuran (THF), dioxane, pyridine, formic acid, acetic acid, trichloroacetic acid, trifluoroacetic acid, hexamethylphosphoramide, carbon sulfide, water; or a mixture thereof.

In certain embodiments, the solvent is a chlorinated hydrocarbon, a nitrile, or a mixture thereof. In other embodiments, the solvent is dichloromethane, acetonitrile or a mixture thereof. In yet other embodiments, the solvent is a mixture of dichloromethane and acetonitrile. In yet other embodiments, the solvent is acetonitrile.

In certain embodiments, the volume ratio of p-toluenesulfonic acid versus acetonitrile is ranging from about 1 to about 100, from about 2 to about 50, from about 5 to about 50, from about 5 to about 25, from about 10 to about 25, or from about 15 to about 25. In certain embodiments, the volume ratio of p-toluenesulfonic acid versus acetonitrile is ranging from about 1 to about 100. In certain embodiments, the volume ratio of p-toluenesulfonic acid versus acetonitrile is ranging from about 2 to about 50. In certain embodiments, the volume ratio of p-toluenesulfonic acid versus acetonitrile is ranging from about 5 to about 50. In certain embodiments, the volume ratio of p-toluenesulfonic acid versus acetonitrile is ranging from about 5 to about 25. In certain embodiments, the volume ratio of p-toluenesulfonic acid versus acetonitrile is ranging from about 10 to about 25. In certain embodiments, the volume ratio of p-toluenesulfonic acid versus acetonitrile is ranging from about 15 to about 25. In certain embodiments, the volume ratio of p-toluenesulfonic acid versus acetonitrile is about 15, about 16, about 17, about 18, about 19, about 20, about 21, about 22, about 23, about 24, or about 25.

In one embodiment, the step of converting (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride to (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) comprises reacting (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride with p-toluenesulfonic acid.

In another embodiment, the step of converting (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride to (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) comprises a solvent.

In certain embodiments, the solvent is petroleum ether, pentane, hexane(s), heptane, octane, isooctane, cyclopentane, cyclohexane, methylcyclohexane, benzene, toluene, xylene, tetralin, cumene, dichloromethane (DCM), 1,2-dichloroethane, 1,1-dichloroethane, 1,2-dichloroethene, chloroform, trichloroethane, trichloroethene, carbon tetrachloride, chlorobenzene, trifluoromethylbenzene, methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, ethyleneglycol, diethyl ether, diisopropyl ether, methyl t-butyl ether (MTBE), diphenyl ether, 1,2-dimethoxyethane, bi(2-methoxyethyl)ether, 1,1-dimethoxymethane, 2,2-dimethoxypropane, anisole, acetone, butanone, methyl ethyl ketone (MEK), methyl isopropyl ketone, methyl butyl ketone, methyl isobutyl ketone (MIBK), methyl acetate, ethyl formate, ethyl acetate, propyl acetate, isopropyl acetate, isobutyl acetate, butyl acetate, ethylene carbonate, propylene carbonate, formamide, N,N-dimethylformamide (DMF), N,N-dimethylacetamide, acetonitrile (ACN), dimethyl sulfoxide (DMSO), sulfolane, nitromethane, nitrobenzene, N-methyl pyrrolindone, 2-methyl tetrahydrofuran, tetrahydrofuran (THF), dioxane, pyridine, formic acid, acetic acid, trichloroacetic acid, trifluoroacetic acid, hexamethylphosphoramide, carbon sulfide, water; or a mixture thereof.

In certain embodiments, the solvent is a hydrocarbon, a nitrile, or a mixture thereof. In other embodiments, the solvent is ethyl acetate, acetonitrile or a mixture thereof. In yet other embodiments, the solvent is ethyl acetate.

In certain embodiments, the step of converting (S)-(2R, 3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride to (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) is performed at a temperature ranging from about 15 to about 70° C., from about 20 to about 70° C., from about 25 to about 70° C. In yet another embodiment, the reaction is performed at a temperature of about 70° C.

In certain embodiments, the molar ratio of the p-toluenesulfonic acid versus (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride is ranging from about 0.1 to about 10, from about 0.2 to about 5, from about 0.5 to about 5, from about 1 to about 4, from about 1 to about 3, or from about 1 to about 2. In certain embodiments, the molar ratio of the p-toluenesulfonic acid versus (S)-(2R,3R,11bR)-3-isobutyl-9,10-dimethoxy-2,3,4, 6,7,11b-hexahydro-1H-pyrido[2,1-a]isoquinolin-2-yl 2-amino-3-methylbutanoate dihydrochloride is ranging from about 1 to about 4. In certain embodiments, the molar ratio of the p-toluenesulfonic acid versus (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride is about 4, about 4.1, about 4.2, about 4.3, about 4.4, or about 4.5. In certain embodiments, the molar ratio of the p-toluenesulfonic acid versus (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride is about 4, about 4.1, or about 4.2. In certain embodiments, the molar ratio of the p-toluenesulfonic acid versus (S)-(2R,3R,11bR)-3-isobutyl-9,10-dimethoxy-2,3,4, 6,7,11b-hexahydro-1H-pyrido[2,1-a]isoquinolin-2-yl 2-amino-3-methylbutanoate dihydrochloride is about 4. In certain embodiments, the molar ratio of the p-toluenesulfonic acid versus (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride is about 4.1. In certain embodiments, the molar ratio of the p-toluenesulfonic acid versus (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride is about 4.2. In some embodiments, the molar ratio of the p-toluenesulfonic acid versus (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride is about 4.5. In certain embodiments, the molar ratio of the p-toluenesulfonic acid versus (S)-(2R,3R, 11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride is ranging from about 1 to about 3. In certain embodiments, the molar ratio of the p-toluenesulfonic acid versus (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride is ranging from about 1 to about 2. In certain embodiments, the molar ratio of the p-toluenesulfonic acid versus (S)-(2R,3R, 11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride is about 2, about 2.1, about 2.2, about 2.3, about 2.4, or about 2.5. In certain embodiments, the molar ratio of the p-toluenesulfonic acid versus (S)-(2R,3R, 11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride is about 2, about 2.1, or about 2.2. In certain embodiments, the molar ratio of the p-toluenesulfonic acid versus (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride is about 2. In certain embodiments, the molar ratio of the p-toluenesulfonic acid versus (S)-(2R,3R,11bR)-3-isobutyl-9,10-dimethoxy-2,3,4,6,7,11b-hexahydro-1H-pyrido[2,1-a] isoquinolin-2-yl 2-amino-3-methylbutanoate dihydrochloride is about 2.1. In certain embodiments, the molar ratio of the p-toluenesulfonic acid versus (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride is about 2.2. In some embodiments, the molar ratio of the p-toluenesulfonic acid versus (S)-(2R,3R, 11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride is about 2.5.

In another embodiment, the reaction of (S)-(2R,3R, 11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride with p-toluenesulfonic acid is performed at a temperature ranging from about 0 to about 100° C., from about 5 to about 90° C., from about 5 to about 80° C., from about 10 to about 70° C., from about 10 to about 60° C., from about 10 to about 50° C., from about 10 to about 40° C., from about 10 to about 30° C. In some embodiments, the reaction of(S)-(2R,3R,11bR)-3-isobutyl-9,10-dimethoxy-2,3,4,6,7,11b-hexahydro-1H-pyrido[2,1-a] isoquinolin-2-yl 2-amino-3-methylbutanoate dihydrochloride with p-toluenesulfonic acid is performed at a temperature ranging from about 20 to about 60° C., from about 30 to about 60° C., from about 40 to about 60° C., from about 50 to about 60° C. In yet other embodiments, the reaction of (S)-(2R,3R,11bR)-3-isobutyl-9,10-dimethoxy-2, 3,4,6,7,11b-hexahydro-1H-pyrido[2,1-a]isoquinolin-2-yl 2-amino-3-methylbutanoate dihydrochloride with p-toluenesulfonic acid is performed at a temperature ranging from about 40 to about 50° C., from about 45 to about 50° C., from about 40 to about 55° C., from about 45 to about 55° C. In another embodiment, the reaction of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride with p-toluenesulfonic acid is performed at a temperature of about 50° C.

In one embodiment, the step of converting (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride to (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) comprises isolating (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride.

In yet another embodiment, the step of converting (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride to (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) is conducted without isolation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride.

In certain embodiments, (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable solvate, hydrate, or polymorph thereof prepared by the methods provided herein has a purity of no less than about 95% by weight, no less than about 96% by weight, no less than about 97% by weight, no less than about 97.5% by weight, no less than about 98% by weight, no less than about 98.5% by weight, no less than about 99% by weight, no less than about 99.5% by weight, no less than about 99.6% by weight, no less than about 99.7% by weight, no less than about 99.8% by weight, or no less than about 99.9% by weight.

In other embodiments, provided herein is a method for preparing (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable solvate, hydrate, or polymorph thereof, with at least about 95% purity; comprising the step of reacting (S)-(2R,3R,1 bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate under conditions suitable to form (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride, via a deprotection step, before the step of reacting (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride with a base.

In other embodiments, provided herein is a method for preparing (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable solvate, hydrate, or polymorph thereof, with at least about 95% purity; comprising the step of reacting (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate under conditions suitable to form (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride, via a deprotection step, before the step of reacting (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride with p-toluenesulfonic acid.

In some embodiments, the deprotection step of (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate is conducted in the presence of an acid. In certain embodiments, the acid is an inorganic acid. In some embodiments, the acid comprises a solution of hydrogen chloride. In some embodiments, the acid comprises a solution of hydrogen chloride in an ether. In some embodiments, the acid comprises a solution of hydrogen chloride in dioxane.

In some embodiments, the deprotection step of (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate is conducted in the presence of a solvent.

In some embodiments, the solvent is an hydrocarbon, chlorinated hydrocarbon, alcohol, ether, ketone, ester, carbonate, amide, nitrile, sulfoxide, sulfone, nitro compound, heteroarene, heterocycle, carboxylic acid, phosphoramide, carbon sulfide, water, or a mixture thereof. In certain embodiments, the solvent is a chlorinated hydrocarbon. In certain embodiments, the solvent is dichloromethane.

In certain embodiments, deprotection step of (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate is performed at a temperature ranging from about 0 to about 25° C., from about 0 to about 30° C., from about 5 to about 25° C., from about 5 to about 20° C. In some embodiments, the reaction is performed at a temperature ranging from about 20 to about 30° C. In yet other embodiments, the reaction is performed at a temperature of about 25° C.

In some embodiments, the reaction of (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate to form (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride, further comprises the step of adding a base.

In certain embodiments, the base comprises an inorganic base. In some embodiments, the bases comprises a carbonate base. In some embodiments, the base comprises sodium carbonate, sodium hydrogen carbonate, potassium carbonate, or potassium hydrogen carbonate. In some embodiments, the base is sodium hydrogen carbonate.

In yet another embodiment, the reaction of (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate to form (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride, further comprises the step of separating the solvent from the aqueous solution. In certain embodiments, the reaction of (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate to form (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride, further comprises the step of adding a second solvent.

In some embodiments, the second solvent is petroleum ether, pentane, hexane(s), heptane, octane, isooctane, cyclopentane, cyclohexane, methylcyclohexane, benzene, toluene, xylene, tetralin, cumene, dichloromethane (DCM), 1,2-dichloroethane, 1,1-dichloroethene, 1,2-dichloroethene, chloroform, trichloroethane, trichloroethene, carbon tetrachloride, chlorobenzene, trifluoromethylbenzene, methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, ethyleneglycol, diethyl ether, diisopropyl ether, methyl t-butyl ether (MTBE), diphenyl ether, 1,2-dimethoxyethane, bi(2-methoxyethyl)ether, 1,1-dimethoxymethane, 2,2-dimethoxypropane, anisole, acetone, butanone, methyl ethyl ketone (MEK), methyl isopropyl ketone, methyl butyl ketone, methyl isobutyl ketone (MIBK), methyl acetate, ethyl formate, ethyl acetate, propyl acetate, isopropyl acetate, isobutyl acetate, butyl acetate, ethylene carbonate, propylene carbonate, formamide, N,N-dimethylformamide (DMF), N,N-dimethylacetamide, acetonitrile (ACN), dimethyl sulfoxide (DMSO), sulfolane, nitromethane, nitrobenzene, N-methyl pyrrolindone, 2-methyl tetrahydrofuran, tetrahydrofuran (THF), dioxane, pyridine, formic acid, acetic acid, trichloroacetic acid, trifluoroacetic acid, hexamethylphosphoramide, carbon sulfide, water; or a mixture thereof.

In certain embodiments, the second solvent is a chlorinated hydrocarbon, a nitrile, or a mixture thereof. In other embodiments, the solvent is dichloromethane, acetonitrile, or a mixture thereof. In yet other embodiments, the solvent is dichloromethane, acetonitrile, or a mixture thereof. In yet other embodiments, the solvent is dichloromethane.

In certain embodiments, the reaction of (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate to form (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride, further comprises the step of adding an acid. In some embodiments, the acid comprises a solution of hydrogen chloride. In some embodiments, the acid comprises a solution of hydrogen chloride in an ether. In some embodiments, the acid comprises a solution of hydrogen chloride in dioxane. In some embodiments, the acid comprises a solution of hydrogen chloride in a $C_{1-6}$ alcohol.

In certain embodiments, the $C_{1-6}$ alcohol is a primary or secondary $C_{1-6}$ alcohol, each optionally substituted with one or more substituents Q. In certain embodiments, the $C_{1-6}$ alcohol is a primary $C_{1-6}$ alcohol, optionally substituted with one or more substituents Q. In certain embodiments, the hydrogen donor is a secondary $C_{1-6}$ alcohol, optionally substituted with one or more substituents Q. In certain embodiments, the hydrogen donor is methanol, ethanol, propan-1-ol, propan-2-ol (IPA), butan-1-ol, butan-2-ol, cyclopentanol, cyclohexanol, benzylalcohol, a menthol, or a mixture thereof. In one embodiment the $C_{1-6}$ alcohol is propan-2-ol.

In some embodiments, the reaction of (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate to form (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride further comprises the step of adding another solvent.

In certain embodiments, the solvent is a chlorinated hydrocarbon, a nitrile, an ester or a mixture thereof. In other embodiments, the solvent is a nitrile. In yet other embodiments, the solvent is acetonitrile.

In certain embodiments, the volume ratio of the hydrogen chloride versus dichloromethane is ranging from about 1 to about 100, from about 2 to about 50, from about 5 to about 50, from about 5 to about 25, from about 10 to about 25, or from about 15 to about 25. In certain embodiments, the volume ratio of hydrogen chloride versus dichloromethane is ranging from about 1 to about 100. In certain embodiments, the volume ratio of hydrogen chloride versus dichloromethane is ranging from about 2 to about 50. In certain embodiments, the volume ratio of hydrogen chloride versus dichloromethane is ranging from about 5 to about 50. In certain embodiments, the volume ratio of the hydrogen chloride versus dichloromethane is ranging from about 5 to about 25. In certain embodiments, the volume ratio of hydrogen chloride versus dichloromethane is ranging from about 10 to about 25. In certain embodiments, the volume ratio of hydrogen chloride versus dichloromethane is ranging from about 15 to about 25. In certain embodiments, the volume ratio of p-toluenesulfonic acid versus acetonitrile is ranging from about 15 to about 25. In certain embodiments, the volume ratio hydrogen chloride versus dichloromethane is about 15, about 16, about 17, about 18, about 19, about 20, about 21, about 22, about 23, about 24, or about 25.

In certain embodiments, the molar ratio of hydrogen chloride versus (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate is ranging from about 0.1 to about 10, from about 0.2 to about 5, from about 0.5 to about 5. In certain embodiments, the molar ratio of hydrogen chloride versus (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate is ranging from about 0.1 to about 5. In certain embodiments, the molar ratio of hydrogen chloride versus (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate is ranging from about 0.2 to about 5. In certain embodiments, the molar ratio of hydrogen chloride versus (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate is ranging from about 0.5 to about 5. In certain embodiments, the molar ratio of hydrogen chloride versus (S)-(2R,3R,11bR)-3-isobutyl-9,10-dimethoxy-2,3,4,6,7,1 1b-hexahydro-1H-pyrido[2,1-a]isoquinolin-2-yl 2-((tert-butoxycarbonyl)amino)-3-methylbutanoate is about 5.1, about 5.2, about 5.3, about 5.4, or about 5.5. In certain embodiments, the molar ratio of hydrogen chloride versus (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate is about 5, about 5.1, or about 5.2. In certain embodiments, the molar ratio of hydrogen chloride versus (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate is about 5. In certain embodiments, the molar ratio of hydrogen chloride versus (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate is about 5.1. In certain embodiments, the molar ratio of hydrogen chloride versus (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate is about 5.2. In some embodiments, the molar ratio of hydrogen chloride versus (S)-(2R,3R,11bR)-3-isobutyl-9,10-dimethoxy-2,3,4,6,7,11b-hexahydro-1H- pyrido[2,1-a]isoquinolin-2-yl 2-((tert-butoxycarbonyl)amino)-3-methylbutanoate is about 5.5.

In certain embodiments, the reaction of (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate to form (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride is conducted at a temperature ranging from about 0 to about 30° C., from about 5 to about 80° C., from about 5 to about 70° C., from about 5 to about 60° C., from about 5 to about 50° C., from about 5 to about 40° C., from about 5 to about 30° C., from about 5 to about 25° C., from about 5 to about 20° C. In some embodiments, the reaction is performed at a temperature ranging from about 5 to about 80° C. In some embodiments, the reaction is performed at a temperature ranging from about 50 to about 70° C.

In other embodiments, the reaction of (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate to form (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride further comprises the step of crystallizing (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride.

In certain embodiments, (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride, or a pharmaceutically acceptable solvate, hydrate, or polymorph thereof prepared by the methods provided herein has a purity of no less than about 95% by weight, no less than about 96% by weight, no less than about 97% by weight, no less than about 97.5% by weight, no less than about 98% by weight, no less than about 98.5% by weight, no less than about 99% by weight, no less than about 99.5% by weight, no less than about 99.6% by weight, no less than about 99.7% by weight, no less than about 99.8% by weight, or no less than about 99.9% by weight.

In yet other embodiments, (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride, or a pharmaceutically acceptable solvate, hydrate, or polymorph thereof prepared by the methods provided herein has a purity of no less than about 99.5%, about 99.6%, about 99.7%, about 99.8%, about 99.9% pure.

In other embodiments, provided herein is a method for preparing (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable solvate, hydrate, or polymorph thereof, with at least about 95% purity; comprising the step of reacting (2R,3R,11bR)-3-isobutyl-9,10-dimethoxy-2,3,4,6,7,1b-hexahydro-1H-pyrido[2,1-a]isoquinolin-2-ol or a salt thereof with a tert-butoxycarbonyl protected amino acid under conditions suitable to form (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate.

In some embodiments, the step of reacting (2R,3R,11bR)-3-isobutyl-9,10-dimethoxy-2,3,4,6,7,11b-hexahydro-1H-pyrido[2,1-a]isoquinolin-2-ol with a tert-butoxycarbonyl protected amino acid to form (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate is conducted using a salt of (2R,3R,11bR)-3-isobutyl-9,10-dimethoxy-2,3,4,6,7,11b-hexahydro-1H-pyrido[2,1-a]isoquinolin-2-ol. In certain embodiments, the salt comprises a sulfonate salt. In yet other embodiments, the salt is a camphorsulfonate salt. In some embodiments, the (2R,3R,11bR)-3-isobutyl-9,10-dimethoxy-2,3,4,6,7,11b-hexahydro-1H-pyrido[2,1-a]isoquinolin-2-ol salt is (2R,3R,11bR)-3-isobutyl-9,10-dimethoxy-2,3,4,6,7,11b-hexahydro-1H-pyrido[2,1-a]isoquinolin-2-ol (S)-(+)-camphorsulfonate.

In certain embodiments, the reaction of (2R,3R,11bR)-3-isobutyl-9,10-dimethoxy-2,3,4,6,7,11b-hexahydro-1H-pyrido[2,1-a]isoquinolin-2-ol or a salt thereof with a tert-butoxycarbonyl protected amino acid to form (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate comprises a valine or alanine aminoacid. In some embodiments, the aminoacid is valine. In yet other embodiments, the tert-butoxycarbonyl protected amino acid is L-valine.

In certain embodiments, the reaction of (2R,3R,11bR)-3-isobutyl-9,10-dimethoxy-2,3,4,6,7,11b-hexahydro-1H-pyrido[2,1-a]isoquinolin-2-ol or a salt thereof to form (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate is conducted in the presence of a base.

In some embodiments, the base is an organic base. In certain embodiments, the base is an inorganic base. In certain embodiments, the base is an organic base. In certain embodiments, the base is sodium hydrogen carbonate, sodium carbonate, sodium citrate, sodium hydroxide, potassium hydroxide, or 4-dimethylaminopyridine. In some embodiments, the base is sodium hydroxide. In some embodiments, the base is potassium hydroxide. In some embodiments, the base is 4-dimethylaminopyridine.

In certain embodiments, the reaction of (2R,3R,11bR)-3-isobutyl-9,10-dimethoxy-2,3,4,6,7,11b-hexahydro-H-pyrido[2,1-a]isoquinolin-2-ol or a salt thereof with a tert-butoxycarbonyl protected amino acid to form (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate further comprises a coupling reagent.

In certain embodiments, the coupling reagent is a carbodiimide, 1,1'-carbonyldiimidazole (CDI), bis(2-oxo-3-oxazolidinyl)phosphinic chloride (BOP—Cl), hexafluorophosphate (BOP reagent), PCh, PCls, or 1-propanephosphonic acid cyclic anhydride. In certain embodiments, the coupling reagent is N-(3-dimethylaminopropyl)-N'-ethylcarbodiimide (EDC or EDCI), N-(3-dimethylaminopropyl)-N'-ethylcarbodiimide hydrochloride (EDC hydrochloride), 1-[3-(dimethylamino)propyl]-3-ethylcarbodiimide methiodide (EDC methiodide), 1-cyclohexyl-3-(2-morpholinoethyl)carbodiimide metho-p-toluenesulfonate, or 1,3-dicyclohexylcarbodiimide (DCC). In certain embodiments, the coupling reagent is N-(3-dimethylaminopropyl)-N'-ethylcarbodiimide (EDC or EDCI), N-(3-dimethylaminopropyl)-N'-ethylcarbodiimide hydrochloride (EDC hydrochloride), 1-[3-(dimethylamino)propyl]-3-ethylcarbodiimide methiodide (EDC methiodide), 1-cyclohexyl-3-(2-morpholinoethyl)carbodiimide metho-p-toluenesulfonate, or 1,3-dicyclohexylcarbodiimide (DCC). In some embodiments, the coupling reagent is N-(3-dimethylaminopropyl)-N'-ethylcarbodiimide (EDC or EDCI).

In certain embodiments, the reaction of (2R,3R,11bR)-3-isobutyl-9,10-dimethoxy-2,3,4,6,7,11b-hexahydro-1H-pyrido[2,1-a]isoquinolin-2-ol or a salt thereof to form (S)-

(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate is conducted in the presence of a solvent.

In some embodiments, the solvent is a hydrocarbon, chlorinated hydrocarbon, alcohol, ether, ester, carbonate, amide, nitrile, sulfoxide, sulfone, nitro compound, heteroarene, heterocycle, water, or a mixture thereof. In certain embodiments, the solvent is a chlorinated hydrocarbon solvent. In certain embodiments the solvent is dichloromethane. In certain embodiments, the solvent is an ether. In some embodiments the solvent is a cycloalkyl ether. In certain embodiments, the solvent is 2-methyltetrahydrofuran (MeTHF).

In certain embodiments, the reaction of (2R,3R,11bR)-3-isobutyl-9,10-dimethoxy-2,3,4,6,7,11b-hexahydro-1H-pyrido[2,1-a]isoquinolin-2-ol or a salt thereof to form (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate is conducted at a temperature ranging from about 0 to about 20° C., from about 0 to about 30° C. from about 5 to about 80° C., from about 5 to about 70° C., from about 5 to about 60° C., from about 5 to about 50° C., from about 5 to about 40° C., from about 5 to about 30° C., from about 5 to about 25° C., from about 5 to about 20° C. In some embodiments, the reaction is performed at a temperature ranging from about 0 to about 20° C.

In some embodiments, (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate prepared by the methods provided herein is obtained as a solution in dichloromethane.

In other embodiments, provided herein is a method for preparing (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable solvate, hydrate, or polymorph thereof, with at least about 95% purity; comprising the step of reacting 3-isobutyl-9,10-dimethoxy-2,3,4,6,7,11b-hexahydro-1H-pyrido[2,1-a]isoquinolin-2-ol with a chiral resolving agent to form (2R,3R,11bR)-3-isobutyl-9,10-dimethoxy-2,3,4,6,7,11b-hexahydro-1H-pyrido[2,1-a]isoquinolin-2-ol or a salt thereof prior to the reaction with a tert-butoxycarbonyl protected amino acid.

In certain embodiments, the chiral agent comprises an amino caprolactamic acid, an amino propanol, anthryl trifluoroethanol, aspartic acid, benzodioxane carboxylic acid, benzylamiocyclohexanemethanol, naphthyl ethylamine, binaphthyl hydrogenphosphate, bis-O-chlorobenxzyl-L-threitol, bis-hydroxyphenyl ethylenediamine, bis-phenylethyl amine, bis-phenylethyl phthalamic acid, bromocamphorsulfonic acid, camphorsulfonic acid, bromophenyl ethylamine, brucine, 2-butanol, camphanic acid, camphoric acid, chloro methylbenzylamine, cinchonidine, cinchonine, dehydroabityl amine, diacetil tartaric acid, dibenzoyl tartaric acid, dibenzyl tartaric acid, diethyl tartrate, diisopropyl tartrate, tartaric acid, quinine, quinic acid, strychnine, N,N-dimethyl phenylethylamine, dimethyl phenyl tetrahydropyrimidine, pyroglutamic acid, phenylpropionic acid, naphthyl ethylsuccinamic acid, naphthylethyl isocyanate, malic acid, mandelic acid, menthyl chloroformate, glutamic acid, or ephedrine. In certain embodiments, the chiral agent comprises an acid. In some embodiments, the acid is a sulfonic acid. In yet other embodiments the acid is a camphorsulfonic acid. In yet other embodiments the acid is (1S)-(+)-camphorsulfonic acid.

In other embodiments, the reaction of 3-isobutyl-9,10-dimethoxy-2,3,4,6,7,11b-hexahydro-1H-pyrido[2,1-a]isoquinolin-2-ol with a chiral resolving agent to form (2R,3R,11bR)-3-isobutyl-9,10-dimethoxy-2,3,4,6,7,11b-hexahydro-1H-pyrido[2,1-a]isoquinolin-2-ol or a salt thereof, is conducted in the presence of a solvent. In some embodiments, the solvent comprises water and an alcohol. In certain embodiments, the alcohol is a $C_{1-6}$ alcohol as defined herein. In yet other embodiments, the solvent mixture comprises water and ethanol. In certain embodiments, the solvent mixture comprises water and ethanol in a volume ratio ranging from about 0.1 to about 100, from about 0.2 to about 50, from about 0.5 to about 25, from about 1 to about 20, from about 1 to about 10, from about 1 to about 5, or from about 1 to about 2. In certain embodiments, the volume ratio of water and ethanol is ranging from about 1 to about 20. In certain embodiments, the volume ratio of water and ethanol is ranging from about 1 to about 19. In certain embodiments, the volume ratio of water and ethanol is ranging from about 1 to about 18. In certain embodiments, the volume ratio of water and ethanol is ranging from about 1 to about 17. In certain embodiments, the volume ratio of water and ethanol is ranging from about 1 to about 16. In certain embodiments, the volume ratio of water and ethanol is ranging from about 1 to about 15. In certain embodiments, the volume ratio of water and ethanol is ranging from about 1 to about 14. In certain embodiments, the volume ratio of water and ethanol is ranging from about 1 to about 13. In certain embodiments, the volume ratio of water and ethanol is ranging from about 1 to about 12. In certain embodiments, the volume ratio of water and ethanol is ranging from about 1 to about 11. In certain embodiments, the volume ratio of water and ethanol is ranging from about 1 to about 10.

In certain embodiments, the reaction of 3-isobutyl-9,10-dimethoxy-2,3,4,6,7,11b-hexahydro-1H-pyrido[2,1-a]isoquinolin-2-ol with a chiral resolving agent to form (2R,3R,11bR)-3-isobutyl-9,10-dimethoxy-2,3,4,6,7,11b-hexahydro-1H-pyrido[2,1-a]isoquinolin-2-ol or a salt thereof, is conducted at a temperature ranging from about 0 to about 100° C., from about 5 to about 90° C., from about 5 to about 80° C., from about 10 to about 70° C., from about 10 to about 60° C., from about 10 to about 50° C., from about 10 to about 40° C., from about 10 to about 30° C. In some embodiments, the reaction of 3-isobutyl-9,10-dimethoxy-2,3,4,6,7,11b-hexahydro-1H-pyrido[2,1-a]isoquinolin-2-ol with a chiral resolving agent to form (2R,3R,11bR)-3-isobutyl-9,10-dimethoxy-2,3,4,6,7,11b-hexahydro-1H-pyrido[2,1-a]isoquinolin-2-ol or a salt thereof, is conducted at a temperature ranging from about 20 to about 80° C., form about 20 to about 70° C., form about 20 to about 60° C., form about 20 to about 70° C. In other embodiments, the reaction is conducted at temperature ranging form about 20 to about 65° C., or form about 20 to about 75° C.

In other embodiments, the reaction of 3-isobutyl-9,10-dimethoxy-2,3,4,6,7,11b-hexahydro-1H-pyrido[2,1-a]isoquinolin-2-ol with a chiral resolving agent to form (2R,3R,11bR)-3-isobutyl-9,10-dimethoxy-2,3,4,6,7,11b-hexahydro-1H-pyrido[2,1-a]isoquinolin-2-ol or a salt thereof further comprises the step of crystallizing (2R,3R,11bR)-3-isobutyl-9,10-dimethoxy-2,3,4,6,7,11b-hexahydro-1H-pyrido[2,1-a]isoquinolin-2-ol or a salt thereof.

In certain embodiments (2R,3R,11bR)-3-isobutyl-9,10-dimethoxy-2,3,4,6,7,11b-hexahydro-1H-pyrido[2,1-a]isoquinolin-2-ol or a pharmaceutically acceptable salt thereof, or solvate, hydrate, or polymorph thereof prepared by the methods provided herein has a purity of no less than about 95% by weight, no less than about 96% by weight, no less than about 97% by weight, no less than about 97.5% by weight, no less than about 98% by weight, no less than about 98.5% by weight, no less than about 99% by weight, no less than about 99.1% by weight, no less than about 99.2% by weight, no less than about 99.3% by weight, no less than about 99.4% by weight, no less than about 99.5% by weight, no less than about 99.6% by weight, no less than about 99.7% by weight, no less than about 99.8% by weight, or no less than about 99.9% by weight.

In certain embodiments, provided herein is a method for preparing (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable solvate, hydrate, or polymorph thereof, with at least about 95% purity; comprising the step of reducing 3-isobutyl-9,10-dimethoxy-3,4,6,7-tetrahydro-1H-pyrido[2,1-a]isoquinolin-2(11bH)-one to form 3-isobutyl-9,10-dimethoxy-2,3,4,6,7,11b-hexahydro-1H-pyrido[2,1-a]isoquinolin-2-ol prior to the reaction with a chiral agent.

In other embodiments, the reduction of 3-isobutyl-9,10-dimethoxy-3,4,6,7-tetrahydro-1H-pyrido[2,1-a]isoquinolin-2(11bR)-one to form 3-isobutyl-9,10-dimethoxy-2,3,4,6,7,11b-hexahydro-1H-pyrido[2,1-a]isoquinolin-2-ol is conducted in the presence of an acid. In some embodiments, the acid comprises a Lewis acid. In other embodiments, the Lewis acid include, but is not limited to, titanium tetrachloride ($TiCl_4$); zinc dichloride ($ZnCl_2$); boron trifluoride ($BF_3$); aluminum and alkylaluminum halides ($AlX_3$ and $R_nAlX_{3-n}$); phosphorus and antimony pentafluorides ($PF_5$ and $SbF_5$); and tin di- and tetrachlorides ($SnCl_2$ and $SnCl_4$); lithium halides (LiX), including lithium chloride and lithium bromide (LiCl and LiBr), copper halides ($CuX_2$), including copper chloride and copper bromide ($CuCl_2$ and $CuBr_2$). In certain embodiments, the acid is lithium halide. In other embodiments, the acid is lithium chloride.

In other embodiments, the reduction of 3-isobutyl-9,10-dimethoxy-3,4,6,7-tetrahydro-1H-pyrido[2,1-a]isoquinolin-2(11bH)-one to form 3-isobutyl-9,10-dimethoxy-2,3,4,6,7,11b-hexahydro-1H-pyrido[2,1-a]isoquinolin-2-ol is conducted in the presence of an organic acid. In certain embodiments, the organic acid is a carboxylic acid. In certain embodiments, the organic acid is a $C_{1-14}$ carboxylic acid optionally substituted with one or more substituents Q. In certain embodiments, the acid is a 2-hydroxy-$C_{1-14}$ carboxylic acid, optionally substituted with one or more substituents Q. In certain embodiments, the hydrogen donor is acetic acid, formic acid, oxalic acid, maleic acid, lactic acid, ascorbic acid, mandelic acid, or a mixture thereof. In certain embodiments, the organic acid is acetic acid.

In some embodiments, the reduction of 3-isobutyl-9,10-dimethoxy-3,4,6,7-tetrahydro-1H-pyrido[2,1-a]isoquinolin-2(11bH)-one to form 3-isobutyl-9,10-dimethoxy-2,3,4,6,7,11b-hexahydro-1H-pyrido[2,1-a]isoquinolin-2-ol is conducted in the presence of a reducing agent. In other embodiments the reducing agent is a borohydride. In certain embodiments the reducing agent is sodium borohydride, lithium borohydride, calcium borohydride, magnesium borohydride, potassium borohydride, 9-BBN, cyano borohydride, bis-triphenylphosphine borohydride, sodium triethyl borohydride, tetrabutylammonium borohydride, tetramethylammonium borohydride, tetraethylammonium borohydride, or lithium triethyl borohydride. In other embodiments the reducing agent is sodium borohydride.

In some embodiments, the reduction of 3-isobutyl-9,10-dimethoxy-3,4,6,7-tetrahydro-1H-pyrido[2,1-a]isoquinolin-2(11bH)-one to form 3-isobutyl-9,10-dimethoxy-2,3,4,6,7,11b-hexahydro-1H-pyrido[2,1-a]isoquinolin-2-ol is conducted in the presence of a solvent. In some embodiments, the solvent comprises dichloromethane and an alcohol. In certain embodiments, the alcohol is a $C_{1-6}$ alcohol as defined herein. In yet other embodiments, the solvent mixture comprises dichloromethane and ethanol. In certain embodiments, the solvent mixture comprises dichloromethane and ethanol in a volume ratio ranging from about 0.1 to about 100, from about 0.2 to about 50, from about 0.5 to about 25, from about 1 to about 20, from about 1 to about 10, from about 1 to about 5, or from about 1 to about 2. In certain embodiments, the volume ratio of dichloromethane and ethanol is ranging from about 2 to about 30. In certain embodiments, the volume ratio of dichloromethane and ethanol is ranging from about 2 to about 20. In certain embodiments, the volume ratio of dichloromethane and ethanol is ranging from about 2 to about 10. In certain embodiments, the volume ratio of dichloromethane and ethanol is ranging from about 2 to about 19, from about 2 to about 18, from about 2 to about 17, from about 2 to about 16, from about 2 to about 15, from about 2 to about 14, from about 2 to about 13, from about 2 to about 12, from about 2 to about 11, from about 2 to about 10. In certain embodiments, the volume ratio of dichloromethane and ethanol is ranging from about 2 to about 14. In certain embodiments, the volume ratio of dichloromethane and ethanol is ranging from about 2 to about 16.

In certain embodiments, the molar ratio of sodium borohydride versus 3-isobutyl-9,10-dimethoxy-3,4,6,7-tetrahydro-1H-pyrido[2,1-a]isoquinolin-2(11bH)-one is ranging from about 0.5 to about 100, from about 1 to about 100, from about 1 to about 50, from about 1 to about 25, from about 1 to about 20, from about 1 to about 10, from about 2 to about 50, from about 5 to about 50, from about 5 to about 25, from about 10 to about 25, or from about 15 to about 25. In certain embodiments, the molar ratio of sodium borohydride versus 3-isobutyl-9,10-dimethoxy-3,4,6,7-tetrahydro-1H-pyrido[2,1-a]isoquinolin-2(11bH)-one is ranging from about 1 to about 100. In certain embodiments, the molar ratio of sodium borohydride versus 3-isobutyl-9,10-dimethoxy-3,4,6,7-tetrahydro-1H-pyrido[2,1-a]isoquinolin-2(11bH)-one is ranging from about 1 to about 50. In certain embodiments, the molar ratio of sodium borohydride versus 3-isobutyl-9,10-dimethoxy-3,4,6,7-tetrahydro-H-pyrido[2,1-a]isoquinolin-2(11bH)-one is ranging from about 1 to about 25. In certain embodiments, the molar ratio of sodium borohydride versus 3-isobutyl-9,10-dimethoxy-3,4,6,7-tetrahydro-H-pyrido[2,1-a]isoquinolin-2(11bH)-one is ranging from about 1 to about 20. In certain embodiments, the molar ratio of sodium borohydride versus 3-isobutyl-9,10-dimethoxy-3,4,6,7-tetrahydro-1H-pyrido[2,1-a]isoquinolin-2(11bH)-one is ranging from about 1 to about 10. In certain embodiments, the molar ratio of sodium borohydride versus 3-isobutyl-9,10-dimethoxy-3,4,6,7-tetrahydro-1H-pyrido[2,1-a]isoquinolin-2(11bH)-one is ranging from about 2 to about 50. In certain embodiments, the molar ratio of sodium borohydride versus 3-isobutyl-9,10-dimethoxy-3,4,6,7-tetrahydro-1H-pyrido[2,1-a]isoquinolin-2(11bH)-one is ranging from about 5 to about 50. In certain embodiments, the molar ratio of sodium borohydride versus 3-isobutyl-9,10-dimethoxy-3,4,6,7-tetrahydro-1H-pyrido[2,1-a]isoquinolin-2(11bH)-one is ranging from about 5 to about 25. In certain embodiments, the molar ratio of sodium borohydride versus 3-isobutyl-9,10-dimethoxy-3,4,6,7-tetrahydro-H-pyrido[2,1-a]isoquinolin-2(11bH)-one is ranging from about 10 to about 25. In certain embodiments, the molar ratio of sodium borohydride versus 3-isobutyl-9,10-dimethoxy-3,4,6,7-tetrahydro-1H-pyrido[2,1-a]isoquinolin-2(11bH)-one is ranging from about 15 to about 25. In certain embodiments, the molar ratio of sodium borohydride versus 3-isobutyl-9,10-dimethoxy-3,4,6,7-tetrahydro-1H-pyrido[2,1-a]isoquinolin-2(11bH)-one is about 1, about 1.1, about 1.2, about 1.3, about 1.4, about 1.5, about 1.6, about 1.7, about 1.8, about 1.9, or about 2.0. In certain embodiments, the molar ratio of sodium borohydride versus 3-isobutyl-9,10-dimethoxy-3,4,6,7-tetrahydro-1H-pyrido[2,1-a]isoquinolin-2(11bH)-one is about 1.2.

In certain embodiments, the molar ratio of acetic acid versus 3-isobutyl-9,10-dimethoxy-3,4,6,7-tetrahydro-1H-pyrido[2,1-a]isoquinolin-2(11bH)-one is ranging from about 0.5 to about 100, from about 1 to about 100, from about 1 to about 50, from about 1 to about 25, from about 1 to about 20, from about 1 to about 10, from about 2 to about 50, from about 5 to about 50, from about 5 to about 25, from about 10 to about 25, or from about 15 to about 25. In certain embodiments, the molar ratio of acetic acid versus 3-isobutyl-9,10-dimethoxy-3,4,6,7-tetrahydro-1H-pyrido[2,1-a]isoquinolin-2(11bH)-one is ranging from about 1 to about 100. In some embodiments, the molar ratio of acetic acid versus 3-isobutyl-9,10-dimethoxy-3,4,6,7-tetrahydro-1H-pyrido[2,1-a]isoquinolin-2(11bH)-one is ranging from about 1 to about 50. In certain embodiments, the molar ratio of acetic acid versus 3-isobutyl-9,10-dimethoxy-3,4,6,7-tetrahydro-1H-pyrido[2,1-a]isoquinolin-2(11bH)-one is ranging from about 1 to about 25. In certain embodiments, the molar ratio of acetic acid versus 3-isobutyl-9,10-dimethoxy-3,4,6,7-tetrahydro-1H-pyrido[2,1-a]isoquinolin-2(11bH)-one is ranging from about 1 to about 20. In certain embodiments, the molar ratio of acetic acid versus 3-isobutyl-9,10-dimethoxy-3,4,6,7-tetrahydro-1H-pyrido[2,1-a]isoquinolin-2(11bH)-one is ranging from about 1 to about 10. In certain embodiments, the molar ratio of acetic acid versus 3-isobutyl-9,10-dimethoxy-3,4,6,7-tetrahydro-1H-pyrido[2,1-a]isoquinolin-2(11bH)-one is ranging from about 2 to about 50. In certain embodiments, the molar ratio of acetic acid versus 3-isobutyl-9,10-dimethoxy-3,4,6,7-tetrahydro-1H-pyrido[2,1-a]isoquinolin-2(11bH)-one is ranging from about 5 to about 50. In certain embodiments, the molar ratio of acetic acid versus 3-isobutyl-9,10-dimethoxy-3,4,6,7-tetrahydro-1H-pyrido[2,1-a]isoquinolin-2(11bH)-one is ranging from about 5 to about 25. In certain embodiments, the molar ratio of acetic acid versus 3-isobutyl-9,10-dimethoxy-3,4,6,7-tetrahydro-1H-pyrido[2,1-a]isoquinolin-2(11bH)-one is ranging from about 10 to about 25. In certain embodiments, the molar ratio of acetic acid versus 3-isobutyl-9,10-dimethoxy-3,4,6,7-tetrahydro-1H-pyrido[2,1-a]isoquinolin-2(11bH)-one is ranging from about 15 to about 25. In certain embodiments, the molar ratio of acetic acid versus 3-isobutyl-9,10-dimethoxy-3,4,6,7-tetrahydro-1H-pyrido[2,1-a]isoquinolin-2(11bH)-one is about 1, about 1.1, about 1.2, about 1.3, about 1.4, about 1.5, about 1.6, about 1.7, about 1.8, about 1.9, or about 2.0. In certain embodiments, the molar ratio of acetic acid versus 3-isobutyl-9,10-dimethoxy-3,4,6,7-tetrahydro-1H-pyrido[2,1-a]isoquinolin-2(11bH)-one is about 1.1.

In certain embodiments, the molar ratio of lithium chloride versus 3-isobutyl-9,10-dimethoxy-3,4,6,7-tetrahydro-1H-pyrido[2,1-a]isoquinolin-2(11bH)-one is ranging from about 0.5 to about 100, from about 1 to about 100, from about 1 to about 50, from about 1 to about 25, from about 1 to about 20, from about 1 to about 10, from about 2 to about 50, from about 5 to about 50, from about 5 to about 25, from about 10 to about 25, or from about 15 to about 25. In certain embodiments, the molar ratio of lithium chloride versus 3-isobutyl-9,10-dimethoxy-3,4,6,7-tetrahydro-1H-pyrido[2,1-a]isoquinolin-2(11bH)-one is ranging from about 1 to about 100. In some embodiments, the molar ratio of lithium chloride versus 3-isobutyl-9,10-dimethoxy-3,4,6,7-tetrahydro-1H-pyrido[2,1-a]isoquinolin-2(11bH)-one is ranging from about 1 to about 50. In certain embodiments, the molar ratio of lithium chloride versus 3-isobutyl-9,10-dimethoxy-3,4,6,7-tetrahydro-H-pyrido[2,1-a]isoquinolin-2(11bH)-one from about 1 to about 25. In certain embodiments, the molar ratio of lithium chloride versus 3-isobutyl-9,10-dimethoxy-3,4,6,7-tetrahydro-1H-pyrido[2,1-a]isoquinolin-2(11bH)-one from about 1 to about 20. In certain embodiments, the molar ratio of lithium chloride versus 3-isobutyl-9,10-dimethoxy-3,4,6,7-tetrahydro-1H-pyrido[2,1-a]isoquinolin-2(11bH)-one from about 1 to about 10. In certain embodiments, the molar ratio of lithium chloride versus 3-isobutyl-9,10-dimethoxy-3,4,6,7-tetrahydro-1H-pyrido[2,1-a]isoquinolin-2(11bH)-one from about 2 to about 50. In certain embodiments, the molar ratio of lithium chloride versus 3-isobutyl-9,10-dimethoxy-3,4,6,7-tetrahydro-1H-pyrido[2,1-a]isoquinolin-2(11bH)-one is ranging from about 5 to about 50. In certain embodiments, the molar ratio of lithium chloride versus 3-isobutyl-9,10-dimethoxy-3,4,6,7-tetrahydro-1H-pyrido[2,1-a]isoquinolin-2(11bH)-one is ranging from about 5 to about 25. In certain embodiments, the molar ratio of lithium chloride versus 3-isobutyl-9,10-dimethoxy-3,4,6,7-tetrahydro-1H-pyrido[2,1-a]isoquinolin-2(11bH)-one is ranging from about 10 to about 25. In certain embodiments, the molar ratio of lithium chloride versus 3-isobutyl-9,10-dimethoxy-3,4,6,7-tetrahydro-1H-pyrido[2,1-a]isoquinolin-2(11bH)-one is ranging from about 15 to about 25. In certain embodiments, the molar ratio of lithium chloride versus 3-isobutyl-9,10-dimethoxy-3,4,6,7-tetrahydro-1H-pyrido[2,1-a]isoquinolin-2(11bH)-one is about 1, about 1.1, about 1.2, about 1.3, about 1.4, about 1.5, about 1.6, about 1.7, about 1.8, about 1.9, or about 2.0. In certain embodiments, the molar ratio of lithium chloride versus 3-isobutyl-9,10-dimethoxy-3,4,6,7-tetrahydro-1H-pyrido[2,1-a]isoquinolin-2(11bH)-one is about 1.

In certain embodiments, the reduction of 3-isobutyl-9,10-dimethoxy-3,4,6,7-tetrahydro-1H-pyrido[2,1-a]isoquinolin-2(11bH)-one to form 3-isobutyl-9,10-dimethoxy-2,3,4,6,7,11b-hexahydro-1H-pyrido[2,1-a]isoquinolin-2-ol is conducted at a temperature ranging from about minus 5 to about minus 15° C., from about minus 5 to about minus 10° C., from about minus 5 to about minus 5° C., from about minus 5 to about 0° C., from about 0 to about 5° C., from about 0 to about 10° C., from about 0 to about 15° C., from about 0 to about 20° C., from about 0 to about 25° C., from about 5 to about 25° C., from about 5 to about 15° C., from about 5 to about 10° C. In some embodiments, the redaction is performed at a temperature ranging from about minus 5 to about minus 15° C. In certain embodiments, the reduction of 3-isobutyl-9,10-dimethoxy-3,4,6,7-tetrahydro-1H-pyrido[2,1-a]isoquinolin-2(11bH)-one to form 3-isobutyl-9,10-dimethoxy-2,3,4,6,7,11b-hexahydro-1H-pyrido[2,1-a]isoquinolin-2-ol is conducted at a temperature ranging of about minus 20° C., about minus 15° C., about minus 10° C., about minus 5° C. In certain embodiments, the reduction of 3-isobutyl-9,10-dimethoxy-3,4,6,7-tetrahydro-1H-pyrido[2,1-a]isoquinolin-2(11bH)-one to form 3-isobutyl-9,10-dimethoxy-2,3,4,6,7,11b-hexahydro-1H-pyrido[2,1-a]isoquinolin-2-ol is conducted at a temperature ranging of about minus 10° C.

In other embodiments, the reaction of 3-isobutyl-9,10-dimethoxy-3,4,6,7-tetrahydro-1H-pyrido[2,1-a]isoquinolin-2(11bH)-one to form 3-isobutyl-9,10-dimethoxy-2,3,4,6,7, 11b-hexahydro-1H-pyrido[2,1-a]isoquinolin-2-ol further comprises the step of crystallizing 3-isobutyl-9,10-dimethoxy-2,3,4,6,7,11b-hexahydro-1H-pyrido[2,1-a]isoquinolin-2-ol.

In certain embodiments 3-isobutyl-9,10-dimethoxy-2,3,4,6,7,11b-hexahydro-1H-pyrido[2,1-a]isoquinolin-2-ol or a pharmaceutically acceptable salt thereof, or solvate, hydrate, or polymorph thereof prepared by the methods provided herein has a purity of no less than about 95% by weight, no less than about 96% by weight, no less than about 97% by weight, no less than about 97.5% by weight, no less than about 98% by weight, no less than about 98.5% by weight, no less than about 99% by weight. In some embodiments 3-isobutyl-9,10-dimethoxy-2,3,4,6,7,11b-hexahydro-1H-pyrido[2,1-a]isoquinolin-2-ol or a pharmaceutically acceptable salt thereof, or solvate, hydrate, or polymorph thereof prepared by the methods provided herein has a purity of no less than about 97.5% by weight, no less than about 97.6% by weight, no less than about 97.7% by weight, no less than about 97.8% by weight, no less than about 97.9% by weight, no less than about 98.1% by weight, no less than about 98.2% by weight, no less than about 98.3% by weight, no less than about 98.4% by weight, no less than about 98.5% by weight, no less than about 98.6% by weight, no less than about 98.7% by weight, no less than about 98.8% by weight, or no less than about 98.9% by weight. In some embodiments 3-isobutyl-9,10-dimethoxy-2,3,4,6,7,11b-hexahydro-1H-pyrido[2,1-a]isoquinolin-2-ol or a pharmaceutically acceptable salt thereof, or solvate, hydrate, or polymorph thereof prepared by the methods provided herein has a purity of no less than about 97.6% by weight, or no less than about 98.1% by weight.

In certain embodiments, provided herein is a method for preparing (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable solvate, hydrate, or polymorph thereof, with at least about 95% purity; comprising the step of reacting 6,7-dimethoxy-3,4-dihydroisoquinoline or a salt thereof with 3-((dimethylamino)methyl)-5-methylhexan-2-one or a salt thereof to form 3-isobutyl-9,10-dimethoxy-3,4,6,7-tetrahydro-1H-pyrido[2,1-a]isoquinolin-2(11bH)-one prior to the reduction step.

In some embodiments, the reaction of 6,7-dimethoxy-3,4-dihydroisoquinoline or a salt thereof with 3-((dimethylamino)methyl)-5-methylhexan-2-one or a salt thereof to form 3-isobutyl-9,10-dimethoxy-3,4,6,7-tetrahydro-1H-pyrido[2,1-a]isoquinolin-2(11bH)-one is conducted in the presence of a solvent.

In some embodiments, the solvent is an hydrocarbon, chlorinated hydrocarbon, alcohol, ether, ketone, ester, carbonate, amide, nitrile, sulfoxide, sulfone, nitro compound, heteroarene, heterocycle, carboxylic acid, phosphoramide, carbon sulfide, water, or a mixture thereof.

In certain embodiments, the solvent is petroleum ether, pentane, hexane(s), heptane, octane, isooctane, cyclopentane, cyclohexane, methylcyclohexane, benzene, toluene, xylene, tetralin, cumene, dichloromethane (DCM), 1,2-dichloroethane, 1,1-dichloroethene, 1,2-dichloroethene, chloroform, trichloroethane, trichloroethene, carbon tetrachloride, chlorobenzene, trifluoromethylbenzene, methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, ethyleneglycol, diethyl ether, diisopropyl ether, methyl t-butyl ether (MTBE), diphenyl ether, 1,2-dimethoxyethane, bi(2-methoxyethyl)ether, 1,1-dimethoxymethane, 2,2-dimethoxypropane, anisole, acetone, butanone, methyl ethyl ketone (MEK), methyl isopropyl ketone, methyl butyl ketone, methyl isobutyl ketone (MIBK), methyl acetate, ethyl formate, ethyl acetate, propyl acetate, isopropyl acetate, isobutyl acetate, butyl acetate, ethylene carbonate, propylene carbonate, formamide, N,N-dimethylformamide (DMF), N,N-dimethylacetamide, acetonitrile (ACN), dimethyl sulfoxide (DMSO), sulfolane, nitromethane, nitrobenzene, N-methyl pyrrolindone, 2-methyl tetrahydrofuran, tetrahydrofuran (THF), dioxane, pyridine, formic acid, acetic acid, trichloroacetic acid, trifluoroacetic acid, hexamethylphosphoramide, carbon sulfide, water; or a mixture thereof.

In certain embodiments, the solvent in the reaction of 6,7-dimethoxy-3,4-dihydroisoquinoline or a salt thereof with 3-((dimethylamino)methyl)-5-methylhexan-2-one or a salt thereof to form 3-isobutyl-9,10-dimethoxy-3,4,6,7-tetrahydro-1H-pyrido[2,1-a]isoquinolin-2(11bH)-one comprises a mixture of an hydrocarbon and water. In certain embodiments, the solvent comprises a mixture of heptane and water.

In certain embodiments, the solvent mixture comprises heptane and water in a volume ratio ranging from about 0.1 to about 100, from about 0.2 to about 50, from about 0.5 to about 25, from about 1 to about 20, from about 1 to about 10, from about 1 to about 5, from about 1 to about 3, or from about 1 to about 2. In certain embodiments, the volume ratio of heptane and water is ranging from about 2 to about 30. In certain embodiments, the volume ratio of heptane and water is ranging from about 2 to about 20. In certain embodiments, the volume ratio of heptane and water is ranging from about 2 to about 10. In certain embodiments, the volume ratio of heptane and water is ranging from about 1 to about 2, from about 1 to about 2, from about 1 to about 5, from about 1.1 to about 2, from about 1.1 to about 3, from about 1.2 to about 2, from about 1.2 to about 3, from about 1.3 to about 2, from about 1.3 to about 3, from about 1.4 to about 2, from about 1.4 to about 3, from about 1.5 to about 2, from about 1.5 to about 3. In certain embodiments, the volume ratio of heptane and water is ranging from about 1.5 to about 3.

In certain embodiments, the molar ratio of 6,7-dimethoxy-3,4-dihydroisoquinoline or a salt thereof versus 3-((dimethylamino)methyl)-5-methylhexan-2-one is ranging from about 0.5 to about 100, from about 1 to about 100, from about 1 to about 50, from about 1 to about 25, from about 1 to about 20, from about 1 to about 10, from about 2 to about 50, from about 5 to about 50, from about 5 to about 25, from about 10 to about 25, or from about 15 to about 25. In certain embodiments, the molar ratio of 6,7-dimethoxy-3,4-dihydroisoquinoline or a salt thereof versus 3-((dimethylamino)methyl)-5-methylhexan-2-one is ranging from about 1 to about 100. In certain embodiments, the molar ratio of 6,7-dimethoxy-3,4-dihydroisoquinoline or a salt thereof versus 3-((dimethylamino)methyl)-5-methylhexan-2-one is ranging from about 1 to about 50. In certain embodiments, the molar ratio of 6,7-dimethoxy-3,4-dihydroisoquinoline or a salt thereof versus 3-((dimethylamino)methyl)-5-methylhexan-2-one is ranging from about 1 to about 25. In certain embodiments, the molar ratio of 6,7-dimethoxy-3,4-dihydroisoquinoline or a salt thereof versus 3-((dimethylamino)methyl)-5-methylhexan-2-one is ranging from about 1 to about 20. In certain embodiments, the molar ratio of 6,7-dimethoxy-3,4-dihydroisoquinoline or a salt thereof versus 3-((dimethylamino)methyl)-5-methylhexan-2-one is ranging from about 1 to about 10. In certain embodiments, the molar ratio of 6,7-dimethoxy-3,4-dihydroisoquinoline or a salt thereof versus 3-((dimethylamino)methyl)-5-methylhexan-2-one is ranging from about 2 to about 50. In certain embodiments, the molar ratio of 6,7-dimethoxy-3,4-dihydroisoquinoline or a salt thereof versus 3-((dimethylamino)methyl)-5-methylhexan-2-one is ranging is ranging from about 5 to about 50. In certain embodiments, the molar ratio of 6,7-dimethoxy-3,4-dihydroisoquinoline or a salt thereof versus 3-((dimethylamino)methyl)-5-methylhexan-2-one is ranging is ranging from about 5 to about 25. In certain embodiments, the molar ratio of 6,7-dimethoxy-3,4-dihydroisoquinoline or a salt thereof versus 3-((dimethylamino)methyl)-5-methylhexan-2-one is ranging from about 10 to about 25. In certain embodiments, the molar ratio of 6,7-dimethoxy-3,4-dihydroisoquinoline or a salt thereof versus 3-((dimethylamino)methyl)-5-methylhexan-2-one is ranging from about 15 to about 25. In certain embodiments, the molar ratio of 6,7-dimethoxy-3,4-dihydroisoquinoline or a salt thereof versus 3-((dimethylamino)methyl)-5-methylhexan-2-one is about 1, about 1.1, about 1.2, about 1.3, about 1.4, about 1.5, about 1.6, about 1.7, about 1.8, about 1.9, or about 2.0. In certain embodiments, the molar ratio of sodium borohydride versus 3-isobutyl-9,10-dimethoxy-3,4,6,7-tetrahydro-1H-pyrido[2,1-a]isoquinolin-2(11bH)-one is about 1.1.

In some embodiments, the reaction of 6,7-dimethoxy-3,4-dihydroisoquinoline or a salt thereof with 3-((dimethylamino)methyl)-5-methylhexan-2-one or a salt thereof to form 3-isobutyl-9,10-dimethoxy-3,4,6,7-tetrahydro-1H-pyrido[2,1-a]isoquinolin-2(11bH)-one is conducted at a temperature ranging from about 0 to about 100° C., from about 5 to about 90° C., from about 5 to about 80° C., from about 10 to about 70° C., from about 10 to about 60° C., from about 10 to about 50° C., from about 10 to about 40° C., from about 10 to about 30° C. In some embodiments, the reaction of 6,7-dimethoxy-3,4-dihydroisoquinoline or a salt thereof with 3-((dimethylamino)methyl)-5-methylhexan-2-one or a salt thereof to form 3-isobutyl-9,10-dimethoxy-3,4,6,7-tetrahydro-1H-pyrido[2,1-a]isoquinolin-2(11bH)-one or a salt thereof, is conducted at a temperature ranging from about 20 to about 80° C., form about 20 to about 70° C., form about 20 to about 60° C., form about 20 to about 50° C. In other embodiments, the reaction is conducted at temperature ranging form about 30 to about 80° C., form about 30 to about 70° C., form about 30 to about 60° C., form about 30 to about 40° C., form about 30 to about 50° C. In some embodiments, the reaction of 6,7-dimethoxy-3,4-dihydroisoquinoline or a salt thereof with 3-((dimethylamino)methyl)-5-methylhexan-2-one or a salt thereof to form 3-isobutyl-9,10-dimethoxy-3,4,6,7-tetrahydro-1H-pyrido[2,1-a]isoquinolin-2(11bH)-one or a salt thereof, is conducted at a temperature ranging from about 30 to about 40° C.

In certain embodiments, the reaction of 6,7-dimethoxy-3,4-dihydroisoquinoline or a salt thereof with 3-((dimethylamino)methyl)-5-methylhexan-2-one or a salt thereof to form 3-isobutyl-9,10-dimethoxy-3,4,6,7-tetrahydro-1H-pyrido[2,1-a]isoquinolin-2(11bH)-one further comprises the step of reacting 3-((dimethylamino)methyl)-5-methylhexan-2-one salt with a base prior to the reaction with 6,7-dimethoxy-3,4-dihydroisoquinoline or a salt thereof.

In some embodiments, the 6,7-dimethoxy-3,4-dihydroisoquinoline salt comprises an inorganic acid salt. In certain embodiments, the inorganic acid salt comprises hydrogen chloride.

In some embodiments, the 3-((dimethylamino)methyl)-5-methylhexan-2-one salt comprises a carboxylic acid salt. In certain embodiments, the carboxylic acid salt comprises a fumarate, oxalate, citrate, or maleic salt. In other embodiments, the carboxylic acid salt comprises an oxalate or citrate salt.

In some embodiments, the reaction of 3-((dimethylamino)methyl)-5-methylhexan-2-one salt with a base comprises an inorganic base. In yet other embodiments, the base is a carbonate, hydrogen carbonate or hydroxide base. In other embodiments, the base is sodium carbonate.

In some embodiments, provided herein is a method for preparing (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable solvate, hydrate, or polymorph thereof, with at least about 95% purity; comprising the steps of (a) converting (2R,3R,11bR)-3-isobutyl-9,10-dimethoxy-2,3,4,6,7,11b-hexahydro-1H-pyrido[2,1-a]isoquinolin-2-ol or a salt thereof to (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride; and (b) converting (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride to (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) or a pharmaceutically acceptable solvate, hydrate, or polymorph thereof.

In certain embodiments, steps (a) (i.e., converting (2R,3R,11bR)-3-isobutyl-9,10-dimethoxy-2,3,4,6,7,1 b-hexahydro-H-pyrido[2,1-a]isoquinolin-2-ol or a salt thereof to (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride) and (b) (i.e., converting (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride to (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate)) are performed as described herein.

In other embodiments, provided herein is a method for preparing (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable solvate, hydrate, or polymorph thereof, with at least about 95% purity; comprising the steps of (a) reacting (2R,3R,11bR)-3-isobutyl-9,10-dimethoxy-2,3,4,6,7,11b-hexahydro-1H-pyrido[2,1-a]isoquinolin-2-ol or a salt thereof with a suitable protected L-valine to form (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate; (b) deprotecting (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate to form (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride, or a pharmaceutically acceptable solvate, hydrate, or polymorph thereof; and (c) converting (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride to (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) or a pharmaceutically acceptable solvate, hydrate, or polymorph thereof.

In certain embodiments, steps (b) (i.e., deprotecting (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate) and (c) (i.e., converting (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride to (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate)) are performed as described herein.

A method for preparing (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable solvate, hydrate, or polymorph thereof, with at least about 95% purity; comprising the steps of (a) crystallizing (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride; (b) reacting (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride, or a pharmaceutically acceptable solvate, hydrate, or polymorph thereof, with a base; and (c) reacting the product of step (b) with p-toluenesulfonic acid to form (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) or a pharmaceutically acceptable solvate, hydrate, or polymorph thereof.

In some embodiments the crystallization step of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride is performed as described herein.

In other embodiments the crystallization step of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride is performed as described in U.S. Provisional App. No. 62/249,074, filed Oct. 30, 2015; the disclosure of which is incorporated herein by reference in its entirety.

In certain embodiments, (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride, or a pharmaceutically acceptable solvate, hydrate, or polymorph thereof prepared by the methods provided herein is substantially pure. In certain embodiments, (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride, or a pharmaceutically acceptable solvate, hydrate, or polymorph thereof prepared by the methods provided herein is suitable for use in humans, such as for treating, preventing, and/or managing a disease, disorder, or condition.

In certain embodiments, the overall yield of the methods provided herein for the preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable solvate, hydrate, or polymorph thereof, is no less than about 30%, no less than about 40%, no less than about 50%, no less than about 55%, no less than about 60%, no less than about 65%, no less than about 70%, no less than about 75%, no less than about 80%, no less than about 85%, no less than about 90%, or no less than about 95%, wherein the yield is calculated based on starting material.

In certain embodiments, (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable solvate, hydrate, or polymorph thereof prepared by the methods provided herein is substantially pure. In certain embodiments, (S)-(2R,3R,11bR)-3-isobutyl-9,10-dimethoxy-2,3,4,6,7,11b-hexahydro-H-pyrido[2,1-a]isoquinolin-2-yl 2-amino-3-methylbutanoate di(4-methylbenzenesulfonate), or a pharmaceutically acceptable solvate, hydrate, or polymorph thereof prepared by the methods provided herein is suitable for use in humans, such as for treating, preventing, and/or managing a disease, disorder, or condition.

In certain embodiments, the total impurities in (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable salt, solvate, hydrate, or polymorph thereof prepared by the methods provided herein are no greater than about 5% by weight, no greater than about 4% by weight, no greater than about 3% by weight, no greater than about 2.5% by weight, no greater than about 2% by weight, no greater than about 1.5% by weight, no greater than about 1% by weight, no greater than about 0.5% by weight, or no greater than about 0.1% by weight.

In certain embodiments, the impurity is detectable by HPLC (high performance liquid chromatography). In certain embodiments, the impurity includes, but is not limited to, (2R,3R,11bR)-3-isobutyl-9,10-dimethoxy-2,3,4,6,7,11b-hexahydro-1H-pyrido[2,1-a]isoquinolin-2-ol or a salt thereof, (S)-(2R,3R,11bR)-3-isobutyl-9,10-dimethoxy-2,3,4,6,7,11b-hexahydro-1H-pyrido[2,1-a]isoquinolin-2-yl 2-aminopropanoate, and (S)-(2S,3R,11bR)-3-isobutyl-9,10-dimethoxy-2,3,4,6,7,11b-hexahydro-1H-pyrido[2,1-a]isoquinolin-2-yl 2-amino-3-methylbutanoate. In some embodiments, the impurity is (R)-(2R,3R,11bR)-3-isobutyl-9,10,11b-trimethoxy-2,3,4,6,7,11b-hexahydro-1H-pyrido[2,1-a]isoquinolin-2-yl 2-amino-3-methylbutanoate. In some embodiments, the impurity is 6,7-dimethoxy-3,4-dihydroisoquinoline. In some embodiments, the impurity is (S)-(2R,3R,11bR)-3-isobutyl-9,10-dimethoxy-7-oxo-2,3,4,6,7,11b-hexahydro-1H-pyrido[2,1-a]isoquinolin-2-yl 2-amino-3-methylbutanoate.

In certain embodiments, the impurity is a metal based impurity. In certain embodiments, the impurity is a volatile organic compound. In certain embodiments, the impurity is an organic solvent. In certain embodiments, the impurity is a sulfonate, dimethylamine, formaldehyde, ethyl chloride, or isopropyl chloride.

In certain embodiments, the weight loss on drying (LOD) of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), or a pharmaceutically acceptable salt, solvate, hydrate, or polymorph thereof prepared by the methods provided herein is no greater than about 5% by weight, no greater than about 4% by weight, no greater than about 3% by weight, no greater than about 2% by weight, no greater than about 1% by weight, no greater than about 0.9% by weight, no greater than about 0.8% by weight, no greater than about 0.7% by weight, no greater than about 0.6% by weight, no greater than about 0.5% by weight, no greater than about 0.4% by weight, no greater than about 0.3% by weight, no greater than about 0.2% by weight, or no greater than about 0.1% by weight.

EXAMPLES

Certain embodiments are illustrated by the following non-limiting examples.

In the examples below, unless otherwise indicated, all temperatures are set forth in degrees Celsius and all parts and percentages are by weight. Reagents may be purchased from commercial suppliers, such as, e.g., Sigma-Aldrich® Chemical Co., and may be used without further purification unless otherwise indicated. Reagents may also be prepared following standard literature procedures known to those skilled in the art. Solvents may be purchased, for example, from Sigma-Aldrich®, and may be used as received or may be purified using standard methods known to those skilled in the art, unless otherwise indicated.

Unless otherwise specified, the reactions set forth below were done generally at ambient temperature or room temperature. Reactions were assayed by HPLC, and terminated as judged by the consumption of starting material.

The compound structures and purities in the examples below were confirmed by one or more of the following methods: proton nuclear magnetic resonance ($^1$H NMR) spectroscopy, $^{13}$C NMR spectroscopy, mass spectroscopy, infrared spectroscopy, melting point, X-ray crystallography, and/or HPLC. $^1$H NMR spectra were determined using a NMR spectrometer operating at a certain field strength. Chemical shifts are reported in parts per million (ppm, δ) downfield from a standard, e.g., an internal standard, such as TMS. Alternatively, $^1$H NMR spectra were referenced to signals from residual protons in deuterated solvents as follows: $CDCl_3$=7.26 ppm; $DMSOd_6$=2.50 ppm; $C_6D_6$=7.16 ppm; $CD_3OD$=3.31 ppm (*J. Org. Chem.* 1997, 62, 7513). Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

Example 1

Preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate)

A. Preparation of 3-isobutyl-9,10-dimethoxy-3,4,6,7-tetrahydro-1H-pyrido[2,1-a]isoquinolin-2(11bH)-one

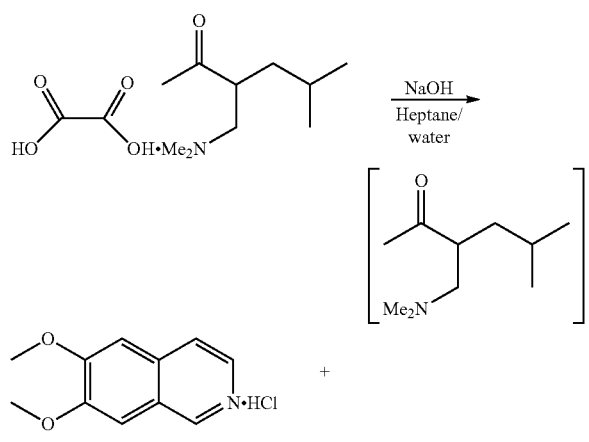

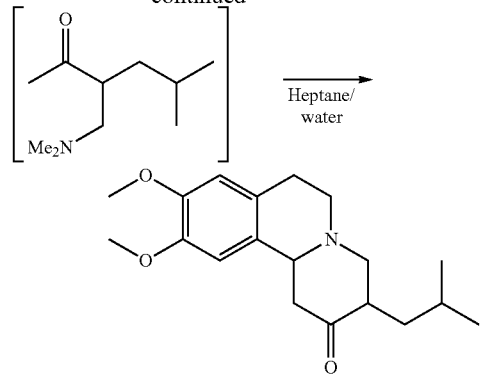

3-((dimethylamino)methyl)-5-methylhexan-2-one oxalate (174 kg) was suspended in a mixture of n-heptane (184 L) and water (757 L). A solution of sodium hydroxide (75.7 kg) in water (908 L) was added, the temperature was stabilized between 15 and 25° C. and the mixture was stirred at this temperature. The pH was adjusted between 8 and 10 by adding the previous solution of sodium hydroxide/water, and the mixture stirred for 30 to 60 minutes. The aqueous layer was then discarded. Alternatively 3-((dimethylamino) methyl)-5-methylhexan-2-one citrate (242.1 kg) was used instead of 3-((dimethylamino)methyl)-5-methylhexan-2-one oxalate and the reaction carried out in the same manner as described herein.

The 3-((dimethylamino)methyl)-5-methylhexan-2-one-heptane solution was added to a solution of 6,7-dimethoxy-3,4-dihydroisoquinoline hydrochloride (126.1 kg) in water (315.2 L) and the mixture was stirred at about 30° C. The reaction was judged to be complete when less than 10%, 6,7-dimethoxy-3,4-dihydroisoquinoline was remaining against a standard solution. The mixture was cooled to room temperature and the solids were filtered, washed with water (176.5 L) then n-heptane (277.4 L) both stabilized at a temperature between 15-20° C., and then dried under vacuum to provide 3-isobutyl-9,10-dimethoxy-3,4,6,7-tetrahydro-1H-pyrido[2,1-a]isoquinolin-2(11bH)-one (139 kg, 79% yield).

A1. Preparation of 3-isobutyl-9,10-dimethoxy-3,4,6,7-tetrahydro-1H-pyrido[2,1-a]isoquinolin-2(11bH)-one starting from 3-((dimethylamino)methyl)-5-methylhexan-2-one Free Base 6,7-dimethoxy-3,4-dihydroisoquinoline hydrochloride (118.2 kg) was dissolved in water (3 volumes). 3-((Dimethylamino)methyl)-5-methylhexan-2-one (99.1 kg) in n-heptane (1.5 volumes) was added and the mixture stirred vigorously for at least 48 hours at about 35° C. until less than 10% 6,7-dimethoxy-3,4-dihydroisoquinoline was remaining against a standard solution. The solid was filtered, washed with water then heptane, and then dried under vacuum to provide 3-isobutyl-9,10-dimethoxy-3,4,6,7-tetrahydro-1H-pyrido[2,1-a]isoquinolin-2(11bH)-one (141.1 kg, 85.6% yield).

B. Preparation of 3-isobutyl-9,10-dimethoxy-2,3,4,6,7,11b-hexahydro-1H-pyrido[2,1-a]isoquinolin-2-ol

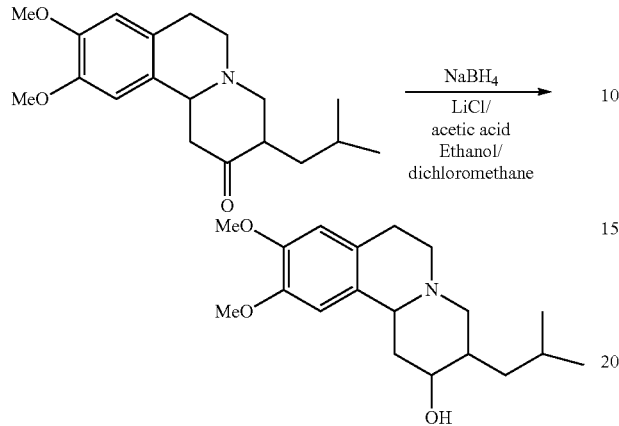

C. Preparation of (2R,3R,11bR)-3-isobutyl-9,10-dimethoxy-2,3,4,6,7,11b-hexahydro-1H-pyrido[2,1-a]isoquinolin-2-ol (S)-(+)-camphorsulfonate

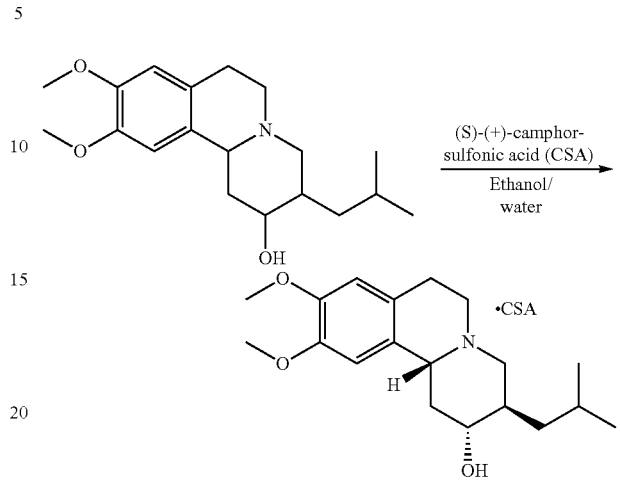

3-isobutyl-9,10-dimethoxy-3,4,6,7-tetrahydro-1H-pyrido[2,1-a]isoquinolin-2(11bH)-one (69.5 kg) was dissolved in dichloromethane (145.9 L, 2.1 volumes). Acetic acid (13.9 L, 1.1 equivalents), lithium chloride (9 kg, 1 equivalent), and ethanol (208.5 L, 14 volumes) were added. The mixture was cooled to −10±5° C. and a solution of sodium borohydride (9.73 kg, 1.2 equivalents) in ethanol (139 L, 5 volumes) was added slowly at −10±5° C. The reaction was stirred for several hours and monitored by HPLC for completion. Once the reaction was complete, the mixture was warmed to 25° C. and a solution of saturated aqueous ammonium chloride (69.5 kg) was added to quench the reaction. The reaction mixture was distilled under vacuum at 40±5° C. to concentrate to minimum volume. Water (139 L) was added and distillation was repeated to minimum volume. Dichloromethane (549 L) and 1N sodium hydroxide (10.4 kg dissolved in 250.2 L of water) were added at 20±5° C., followed by stirring for at least 15 minutes. The layers were allowed to separate and the organic layer was collected, while the water layer was back extracted with dichloromethane. The combined organics were washed with water, separated, and then distilled under vacuum to minimum volume. Isopropyl acetate (347.5 L) was added and the mixture was distilled under vacuum to approximately 3 volumes total and repeated. The slurry was heated to 85±5° C., held for 0.5-1 hour, and then cooled to 65° C. to initiate crystallization. The mixture was further cooled to 20° C. and held for 1 hour. The solids were filtered, rinsed with isopropyl acetate, and then dried under vacuum to provide 3-isobutyl-9,10-dimethoxy-2,3,4,6,7,11b-hexahydro-1H-pyrido[2,1-a]isoquinolin-2-ol (60 kg, 86% yield). Another batch was carried out starting from 3-isobutyl-9,10-dimethoxy-3,4,6,7-tetrahydro-1H-pyrido[2,1-a]isoquinolin-2(11bH)-one (69.5 kg), using the same procedure described herein, to give 3-isobutyl-9,10-dimethoxy-2,3,4,6,7,11b-hexahydro-1H-pyrido[2,1-a]isoquinolin-2-ol (59.7 kg, 85% yield).

3-isobutyl-9,10-dimethoxy-2,3,4,6,7,11b-hexahydro-1H-pyrido[2,1-a]isoquinolin-2-ol (59.8 kg) and (1S)-(+)-camphorsulfonic acid (46 kg, 1 equivalent) were suspended in 19:1 ethanol:water (v/v), which was then heated until a solution was formed at ~75° C. The mixture was cooled to 53±2° C. and held until crystallization occurs. The batch was seeded with (2R,3R,11bR)-3-isobutyl-9,10-dimethoxy-2,3,4,6,7,11b-hexahydro-1H-pyrido[2,1-a]isoquinolin-2-ol (1S)-(+)-camphorsulfonate if nucleation did not occur. The mixture was cooled to 25±5° C. over at least 14 hours. The slurry was filtered, washed with ethanol, and then dried under vacuum to provide (2R,3R,11bR)-3-isobutyl-9,10-dimethoxy-2,3,4,6,7,11b-hexahydro-1H-pyrido[2,1-a]isoquinolin-2-ol (1S)-(+)-camphorsulfonate as a crystalline solid (38.7, 38% yield). Another batch was carried out starting from 3-isobutyl-9,10-dimethoxy-2,3,4,6,7,11b-hexahydro-1H-pyrido[2,1-a]isoquinolin-2-ol (59.6 kg), using the same procedure described herein, to give (2R,3R,11bR)-3-isobutyl-9,10-dimethoxy-2,3,4,6,7,11b-hexahydro-1H-pyrido[2,1-a]isoquinolin-2-ol (1S)-(+)-camphorsulfonate (39.5 kg, 38% yield).

D. Preparation of (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate

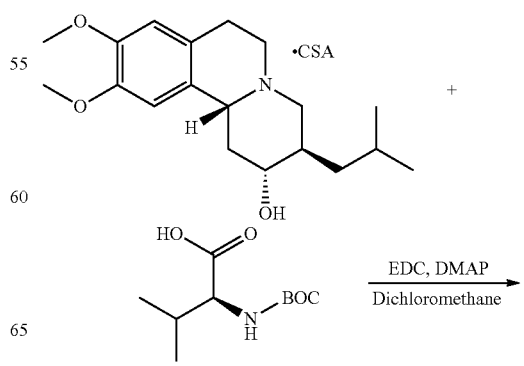

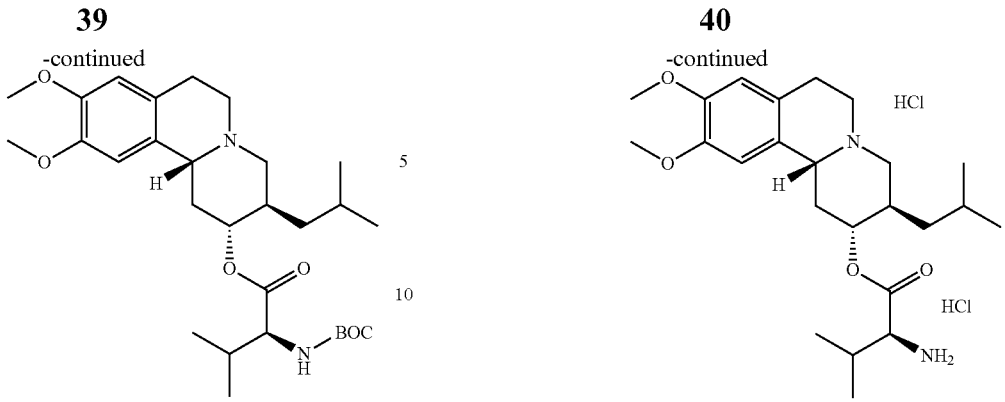

(2R,3R,11bR)-3-isobutyl-9,10-dimethoxy-2,3,4,6,7,11b-hexahydro-1H-pyrido[2,1-a]isoquinolin-2-ol (1S)-(+)-camphorsulfonate (25.9 kg) was dissolved in dichloromethane (129.5 L, 5 volumes) and 1N sodium hydroxide (11.1 kg dissolved in 282.2 L of water) (pH>10), and then the mixture was stirred at 25±5° C. The organics were collected and washed with additional sodium hydroxide solution, and then with water. The organic phase was collected, dried with sodium sulfate, and then filtered to remove the solids. Boc-L-valine (12.2 kg, 1.2 equivalents) and 4-dimethylaminopyridine (1.55 kg, 0.3 equivalents) were charged to the organic phase and the mixture was then cooled to approximately 0° C. N-(3-dimethylaminopropyl)-N'-ethylcarbodiimide hydrochloride (15.8 kg, 1.8 equivalents) was charged and the reaction was stirred for >3 hours. The reaction mixture was kept at 0±5° C. and was monitored by HPLC for completion. Once complete, water was added and the contents were agitated. After settling, the water layer was discharged. The organic layer was washed with aqueous citric acid (prepared from 5.2 kg citric acid in 101 L of water) and then with water, to yield (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate as a solution in dichloromethane.

E. Preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride

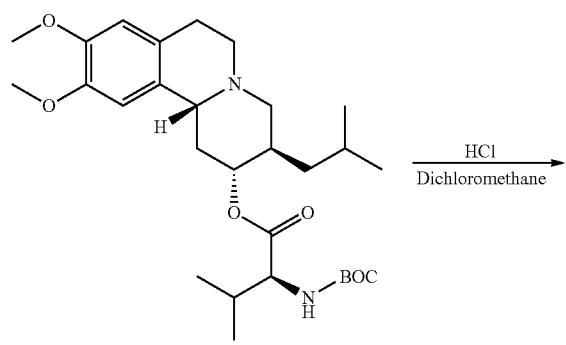

Hydrogen chloride in dioxane (4M, 57 L, 5 equivalents) was slowly added to a solution of (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate in dichloromethane, while maintaining the temperature between 5-10° C. Once addition was complete, the mixture was agitated at 25±5° C. for >12 hours. Upon completion, aqueous sodium bicarbonate (217.6 kg) was slowly added and the mixture was agitated at 25±5° C. until pH>7. The organics were collected and washed with additional aqueous sodium bicarbonate, and then with water. Sodium sulfate was added to the organic layer and the mixture was then filtered to remove the solids. The organic layer was then distilled to the minimum volume required for agitation. Acetonitrile (70 L) was added and the mixture was again distilled down to minimum volume. Acetonitrile was added until the solution was a total of 10 volumes, and then the solution was cooled to 10±5° C. Hydrogen chloride in isopropanol (3.7 M, 26.4 L, 2.1 equivalents) was slowly added, followed by ethyl acetate (57 L) and the mixture was then heated to 50±5° C. Additional ethyl acetate was added followed by (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride seeds and the mixture was heated to 75±5° C. for >1 hour. The slurry was slowly cooled to 25±5° C., and the solids were filtered, washed with ethyl acetate, and then dried under vacuum to yield (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (16.8 kg, 73% yield). Another batch was carried out starting from (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate (24.4 kg), using the same procedure described herein, to give (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (17 kg, 79% yield).

F. Preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate)

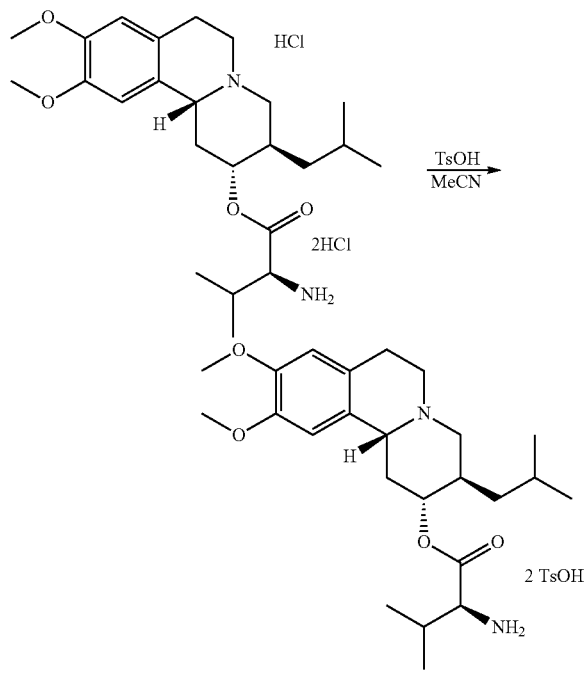

(S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (10.2 kg) was dissolved in dichloromethane (9 volumes) and aqueous sodium bicarbonate. The mixture was stirred at about 25° C. The organics were collected and washed with additional aqueous sodium bicarbonate, and then washed with water. The organic layer was collected and acetonitrile added to the dichloromethane solution. The solution was distilled to the minimum volume required for stirring. Additional acetonitrile was added and the mixture was distilled down to minimum volume. The mixture was tested for moisture content, then warmed to about 50° C. To this mixture, a solution of p-toluenesulfonic acid (2 equivalents) in acetonitrile was slowly added and the contents were agitated for >8 hours at about 50° C. The slurry was then cooled to about 25° C. and the solids filtered, washed with acetonitrile, and then dried under vacuum to yield (S)-(2,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (14.7 kg, 92.8% yield, 99.9% pure).

F1. Preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate)

(S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (15 kg) was suspended in dichloromethane (136.5 L, 9 volumes), aqueous sodium bicarbonate (245 kg) was added until pH>6.5, and then the mixture was agitated at 25±5° C. The organics were collected and washed with additional aqueous sodium bicarbonate, and then washed with water. The solution was then distilled to the minimum volume required for agitation. Acetonitrile (54 L) was added and the mixture was distilled down to minimum volume and repeated. Acetonitrile was added and the mixture was tested for moisture content and, once within the specification it was warmed to 50±5° C. To this mixture, a solution of p-toluenesulfonic acid (11.7 kg, 2 equivalents) in acetonitrile (55.5 L) was slowly added and the contents were agitated for >8 hours at 50±5° C. The slurry was then cooled to 25±5° C. and the solids were filtered, washed with acetonitrile, and then dried under vacuum to yield (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (20.6 kg, 88% yield, ≥98% pure).

G. Preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate)

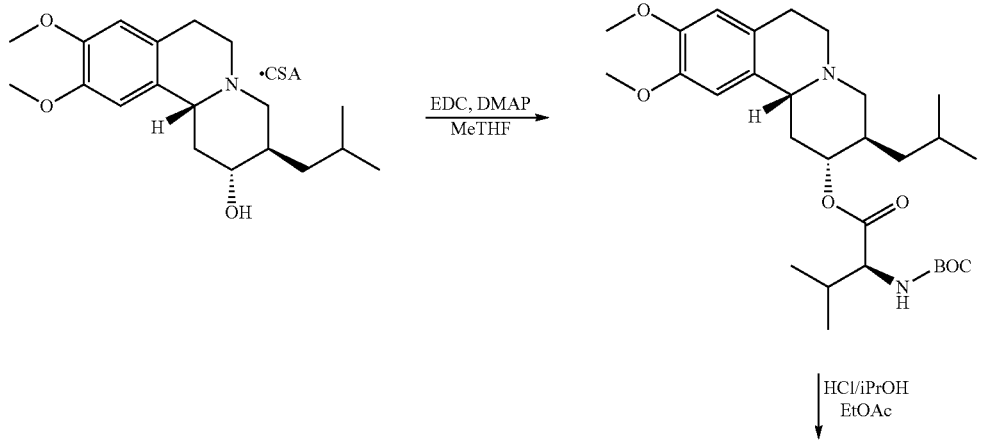

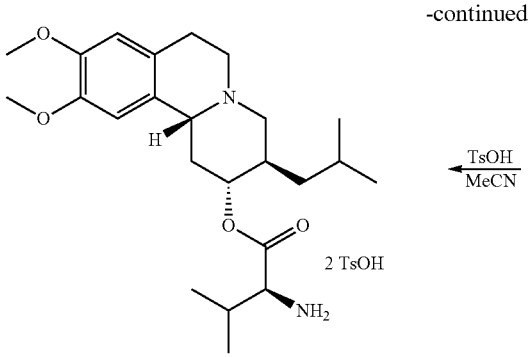 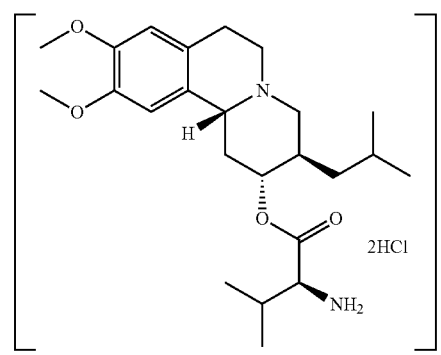

To an Erlenmeyer flask was charged (2R,3R,11bR)-3-isobutyl-9,10-dimethoxy-2,3,4,6,7,11b-hexahydro-1H-pyrido[2,1-a]isoquinolin-2-ol (1S)-(+)-camphorsulfonate (20 g) in 2-methyltetrahydrofuran (MeTHF) (100 mL), followed by aqueous KOH (2 M, 110 mL). The mixture was agitated for 15 min. The resulting biphasic solution was transferred to a separatory funnel and the layers were allowed to separate. An emulsion layer formed which was broken up with brine for better separation. The aqueous layer was discarded. To the organic layer was added $H_2O$ (20 mL) followed by shaking several times. After 15 min, the layers were separated and aqueous layer was discarded.

To a round bottom flask was added the MeTHF solution of the free based material (~100 mL; from above) along with additional MeTHF (40 mL). N-Boc-(L)-Val-OH (1.2 eq.) and DMAP (0.27 eq.) were added, after which a clear yellow solution resulted. The solution was cooled to 0 to −10° C. with an acetone ice/$H_2O$ bath. After reaching temperature, 1-ethyl-3-(3-dimethylaminopropyl)carbodiimide (EDCI) (1.77 eq.) was added and stirring was continued at 0 to −10° C. for 3 h. After 3 h, the ice bath was removed and the reaction was agitated for at least 5 h. The analytical data indicated complete conversion to (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate after 18 h. The reaction was quenched with 5% aqueous citric acid (78 mL) followed by washing the organic layer with $H_2O$ (60 mL). The resulting organic solution consisted of (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate which was carried onto the deprotection step without further purification. In an alternative procedure, (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate was isolated by evaporating the organic solution.

The (S)-(2R,3R,11bR)-3-isobutyl-9,10-dimethoxy-2,3,4,6,7,11b-hexahydro-1H-pyrido[2,1-a]isoquinolin-2-yl 2-((tert-butoxycarbonyl)amino)-3-methylbutanoate solution from above was transferred to a clean round bottom flask, along with additional MeTHF (110 mL). To the solution was added EtOAc (44 mL) and 3.7 N HCl/isopropanol (21 mL; other HCl solutions can be used). The solution was heated to 45° C., seeded with (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride, and stirred for ½ h. After ½ h, more EtOAc (30 mL) was added and the temperature was increased to 70° C. for 1 h. After 1 h, HPLC showed that 8% starting material still remained. To the reaction was added more 3.7 N HCl/isopropanol (3 mL), followed by heating at 70° C. for 2 h. After 2 h, the reaction was complete. Saturated aqueous $NaHCO_3$ (30 mL) was slowly added and the mixture was stirred for ½ h and was then washed with $H_2O$ (60 mL). The resulting solution of freebased material (HPLC>95% purity) was carried onto the tosylate salt formation without further purification.

The free base solution from above was evaporated and a solvent exchange was completed with acetonitrile (2×40 mL). The yellow residue was dissolved in acetonitrile (67 mL) and heated to 45-55° C., after which a solution of p-TsOH/acetonitrile (8.3 g/139 mL) was added in one portion. After stirring for 18 h at 45° C., the slurry was cooled to 25° C., the white solid was filtered and washed with EtOAc (2×10 mL), and then dried in a vacuum oven at 50° C. for 18 h to afford (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (14.5 g, 53% overall isolated yield). The analytical HPLC data confirmed purity (99.68%) and chirality (99.77%).

In an alternative procedure, (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride was isolated by filtration before freebasing and then converted to the ditosylate salt as described above.

H. Preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate)

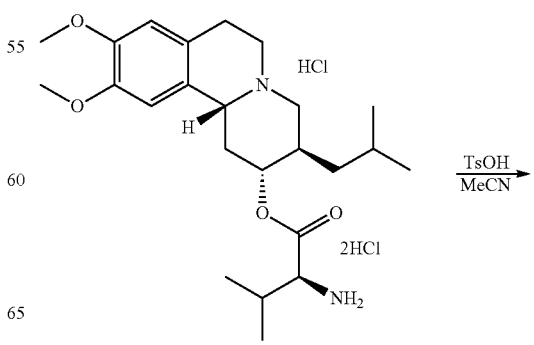

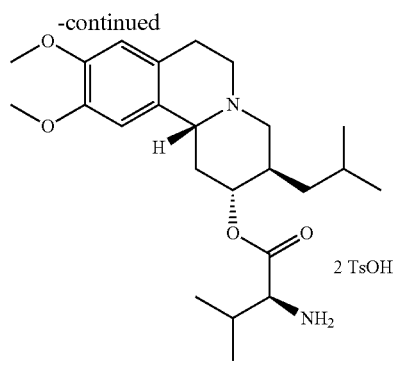

Isolated (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (10 g, 0.02 mol) was suspended in EtOAc (500 mL) and was then heated to 70° C. As the mixture was heating, p-TsOH (14 g, 4 eq.) was added. During heating, the mixture became a clear homogenous solution. The solution was aged for 2-3 h at 70° C. After 2-3 h, a white solid precipitated, and the heating source was removed. The suspension was stirred for 18 h and was then filtered. The solid was washed with EtOAc, and then dried in a vacuum oven at 50° C. for 18 h to afford (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (13.2 g, 88% isolated yield) as a white solid. The H-NMR of the sample matched the one obtained from step G.

The embodiments described herein are intended to be merely exemplary, and those skilled in the art will recognize, or will be able to ascertain using no more than routine experimentation, numerous equivalents of specific compounds, materials, and procedures. All such equivalents are considered to be within the scope of the disclosure.

All of the patents, patent applications and publications referred to herein are incorporated herein in their entireties. Citation or identification of any reference in this application is not an admission that such reference is available as prior art to this application. The full scope of the disclosure is better understood with reference to the appended claims.

What is claimed is:

1. A VMAT2 inhibitor that is (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) having a weight loss on drying (LOD) of no greater than about 5% by weight.

2. The VMAT2 inhibitor of claim 1, having a weight loss on drying (LOD) of no greater than about 4% by weight.

3. The VMAT2 inhibitor of claim 1, having a weight loss on drying (LOD) of no greater than about 3% by weight.

4. The VMAT2 inhibitor of claim 1, having a weight loss on drying (LOD) of no greater than about 2% by weight.

5. The VMAT2 inhibitor of claim 1, having a weight loss on drying (LOD) of no greater than about 1% by weight.

6. The VMAT2 inhibitor of claim 1, having a weight loss on drying (LOD) of no greater than about 0.8% by weight.

7. The VMAT2 inhibitor of claim 1, having a weight loss on drying (LOD) of no greater than about 0.6% by weight.

8. The VMAT2 inhibitor of claim 1, having a weight loss on drying (LOD) of no greater than about 0.4% by weight.

9. The VMAT2 inhibitor of claim 1, having a weight loss on drying (LOD) of no greater than about 0.2% by weight.

10. The VMAT2 inhibitor of claim 1, having a weight loss on drying (LOD) of no greater than about 0.1% by weight.

11. The VMAT2 inhibitor of claim 4, wherein (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) has an impurity profile comprising total impurities in an amount that is no greater than about 4% by weight.

12. The VMAT2 inhibitor of claim 11, wherein the impurity profile comprises total impurities in an amount that is no greater than about 3% by weight.

13. The VMAT2 inhibitor of claim 11, wherein the impurity profile comprises total impurities in an amount that is no greater than about 2.5% by weight.

14. The VMAT2 inhibitor of claim 11, wherein the impurity profile comprises total impurities in an amount that is no greater than about 2% by weight.

15. The VMAT2 inhibitor of claim 11, wherein the impurity profile comprises total impurities in an amount that is no greater than about 1.5% by weight.

16. The VMAT2 inhibitor of claim 11, wherein the impurity profile comprises total impurities in an amount that is no greater than about 1% by weight.

17. The VMAT2 inhibitor of claim 11, wherein the impurity profile comprises total impurities in an amount that is no greater than about 0.5% by weight.

18. The VMAT2 inhibitor of claim 11, wherein the impurity profile comprises total impurities in an amount that is no greater than about 0.1% by weight.

19. The VMAT2 inhibitor of claim 11, wherein the impurity profile comprises one or more impurities chosen from: (2R,3R,11bR)-3-isobutyl-9,10-dimethoxy-2,3,4,6,7,11b-hexahydro-1H-pyrido[2,1-a]isoquinolin-2-ol or a salt thereof, (S)-(2R,3R,11bR)-3-isobutyl-9,10-dimethoxy-2,3,4,6,7,11b-hexahydro-1H-pyrido[2,1-a]isoquinolin-2-yl 2-aminopropanoate, and (S)-(2S,3R,11bR)-3-isobutyl-9,10-dimethoxy-2,3,4,6,7,11b-hexahydro-1H-pyrido[2,1-a]isoquinolin-2-yl 2-amino-3-methylbutanoate.

20. The VMAT2 inhibitor of claim 11, wherein the impurity profile comprises (R)-(2R,3R,11bR)-3-isobutyl-9,10,11b-trimethoxy-2,3,4,6,7,11b-hexahydro-1H-pyrido[2,1-a]isoquinolin-2-yl 2-amino-3-methylbutanoate.

21. The VMAT2 inhibitor of claim 11, wherein the impurity profile comprises 6,7-dimethoxy-3,4-dihydroisoquinoline.

22. The VMAT2 inhibitor of claim 11, wherein the impurity profile comprises (S)-(2R,3R,11bR)-3-isobutyl-9,10-dimethoxy-7-oxo-2,3,4,6,7,11b-hexahydro-1H-pyrido[2,1-a]isoquinolin-2-yl-2-amino-3-methylbutanoate.

23. The VMAT2 inhibitor of claim 11, having an impurity profile comprising one or more impurities chosen from metal-based impurities.

24. The VMAT2 inhibitor of claim 11, having an impurity profile comprising one or more impurities chosen from dimethylamine, formaldehyde, ethyl chloride, and isopropyl chloride.

25. A pharmaceutical composition comprising (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) of claim 1 and a pharmaceutically acceptable carrier.

26. A pharmaceutical composition comprising (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) of claim 3 and a pharmaceutically acceptable carrier.

27. A pharmaceutical composition comprising (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) of claim 11 and a pharmaceutically acceptable carrier.

28. A pharmaceutical composition comprising (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) of claim 14 and a pharmaceutically acceptable carrier.

29. A pharmaceutical composition comprising (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) of claim 19 and a pharmaceutically acceptable carrier.

30. A pharmaceutical composition comprising (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) of claim 24 and a pharmaceutically acceptable carrier.

\* \* \* \* \*